United States Patent
Asano et al.

(10) Patent No.: US 11,071,738 B2
(45) Date of Patent: *Jul. 27, 2021

(54) THERAPEUTIC AGENT FOR FATTY LIVER DISEASES AND THERAPEUTIC AGENT FOR ADIPOSITY

(71) Applicants: Hiroshima University, Higashihiroshima (JP); Tokyo University of Pharmacy & Life Sciences, Hachioji (JP); The University of Tokyo, Tokyo (JP)

(72) Inventors: Tomoichiro Asano, Hiroshima (JP); Yusuke Nakatsu, Hiroshima (JP); Hisanaka Ito, Hachioji (JP); Takayoshi Okabe, Tokyo (JP)

(73) Assignees: Hiroshima University, Higashihiroshima (JP); Tokyo University of Pharmacy & Life Sciences, Hachioji (JP); The University of Tokyo, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 16/636,752

(22) PCT Filed: Aug. 6, 2018

(86) PCT No.: PCT/JP2018/029496
§ 371 (c)(1),
(2) Date: Jun. 30, 2020

(87) PCT Pub. No.: WO2019/031471
PCT Pub. Date: Feb. 14, 2019

(65) Prior Publication Data
US 2020/0383989 A1 Dec. 10, 2020

(30) Foreign Application Priority Data
Aug. 7, 2017 (JP) .............................. JP2017-152807

(51) Int. Cl.
*A61K 31/19* (2006.01)
*A61K 31/415* (2006.01)
(Continued)

(52) U.S. Cl.
CPC ........ *A61K 31/5377* (2013.01); *A61K 31/341* (2013.01); *A61K 31/403* (2013.01);
(Continued)

(58) Field of Classification Search
CPC . A61K 31/192; A61K 31/198; A61K 31/4184
(Continued)

(56) References Cited

U.S. PATENT DOCUMENTS

2016/0199367 A1* 7/2016 Jo ....................... A61K 31/4745
514/288

FOREIGN PATENT DOCUMENTS

CN 102030700 4/2011
EP 3549930 A1 10/2019
(Continued)

OTHER PUBLICATIONS

Stal "Liver fibrosis in non-alcoholic fatty liver disease-diagnostic challenge with prognostic significance," World J. Gastroenterology, 2015, vol. 21, p. 11077-11087 (Year: 2015).*

(Continued)

*Primary Examiner* — Shengjun Wang
(74) *Attorney, Agent, or Firm* — William C. Schrot; Jeffrey I. Auerbach; AuerbachSchrot LLC

(57) ABSTRACT

The purpose of the invention is to develop a novel therapeutic agent for fatty liver diseases such as NASH or NAFLD. The invention provides a therapeutic or prophylactic agent for fatty liver diseases that comprises, as an active ingredient, a compound represented by formula (I) or a pharmaceutically acceptable salt thereof. The invention
(Continued)

also provides a therapeutic or prophylactic agent for adiposity that comprises, as an active ingredient, a compound represented by formula (I) or a pharmaceutically acceptable salt thereof.

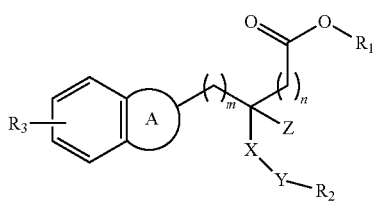

(I)

15 Claims, 4 Drawing Sheets

(51) Int. Cl.
| | |
|---|---|
| A61K 31/5377 | (2006.01) |
| A61P 1/16 | (2006.01) |
| A61P 3/04 | (2006.01) |
| A61K 31/341 | (2006.01) |
| A61K 31/403 | (2006.01) |
| A61K 31/4184 | (2006.01) |
| A61K 31/4439 | (2006.01) |
| A61K 45/06 | (2006.01) |

(52) U.S. Cl.
CPC ........ *A61K 31/415* (2013.01); *A61K 31/4184* (2013.01); *A61K 31/4439* (2013.01); *A61P 1/16* (2018.01); *A61P 3/04* (2018.01); *A61K 45/06* (2013.01)

(58) Field of Classification Search
USPC .................................. 514/569, 394
See application file for complete search history.

(56) References Cited

FOREIGN PATENT DOCUMENTS

| JP | 2014-518543 | 8/2014 |
|---|---|---|
| WO | WO 2002/060436 A2 | 8/2002 |
| WO | WO 2004/087720 A1 | 10/2004 |
| WO | WO 2005/007123 A2 | 1/2005 |
| WO | WO 2005/089316 A2 | 9/2005 |
| WO | WO 2006/040646 A1 | 4/2006 |
| WO | WO 2012/116176 A2 | 8/2012 |
| WO | WO 2012/151958 A1 | 11/2012 |
| WO | WO 2018/101329 A1 | 6/2018 |

OTHER PUBLICATIONS

Potter et al. (2010) *Structure-guided Design of α-amino acid-derived Pin1 inhibitors*, Bioorg Med Chem Lett 20(2):586-590.
Guo et al. (2014) *Structure-based Design of Novel Human Pin1 Inhibitors (III): Optimizing affinity Beyond the Phosphate Recognition Pocket*, Bioorganic & Medicinal Chemistry Letters, 24(17):4187-4191.
Nakagawa et al. (2015) *Peptidyl Prolyl Isomerase Pin1-inhibitory Activity of D-glutamic and D-aspartic Acid Derivatives Bearing a Cyclic Aliphatic Amine Moiety*, Bioorganic & Medicinal Chemistry Letters, 25(23):5619-5624.
Asano T (2013) *Mechanism of insulin resistance and inflammation onset by malformation of proline isomerase Pin1 complex*, Journal of Japan Applied Enzyme Association, No. 48, pp. 39-40.
Yamazaki et al. (2014) *Study of treatment effect of NASH by using Pin1 inhibitor Juglone*, Journal of the Japan Diabetic Society, vol. 57, Supp. 1, S-456.
Mori et al. (2014) *A High-throughput Screen for Inhibitors of the Prolyl Isomerase, Pin1, Identifies a Seaweed Polyphenol that Reduces Adipose Cell Differentiation*, Bioscience Biotechnology and Biochemistry, 78(5):832-838.
Nakatsu et al. (2012) *Role of Pin1 Protein in the Pathogenesis of Nonalcoholic Steatohepatitis in a Rodent Model*, J Biol Chem 287(53):44526-44535.
Potter et al. (2010) *Discovery of Cell-Active Phenyl-Imidazole Pin1 Inhibitors by Structure-Guided Fragment Evolution*, Bioorg Med Chem Lett 20(2):6483-6488.
Dong et al. (2010) *Structure-Based design of novel human Pin1 inhibitors (II)*, Bioorg Med Chem Lett 20(70):2210-2214.
Zhou et al. (2015) *Hepatoprotective effect of juglone on dimethylnitrosamine-induced liver fibrosis and its effect on hepatic antioxidant defense and the expression levels of α-SMA and collagen III*, Mol Med Rep 12(3):4095-4102.
Yang et al. (2014) *Pin1 induction in the fibrotic liver and its roles in TGF-β1 expression and smad2/3 phosphorylation*, J Hepatol 60(6):1235-1241.
Peng et al. (2015) *Juglone prevents metabolic endotoxemia-induced hepatitis and neuroinflammation via suppressing TLR4/NF-κB signaling pathway in high-fat diet rats*, Biochem Biophys Res Commun 462(3):245-250.

* cited by examiner (A)

Normal diet (B)

HFDT (C)

HFDT + H-163

THERAPEUTIC AGENT FOR FATTY LIVER DISEASES AND THERAPEUTIC AGENT FOR ADIPOSITY

CROSS-REFERENCE TO RELATED APPLICATIONS

This application is a § 371 Application of PCT/JP2018/029496 (filed on Aug. 6, 2018), which application claims priority to Japanese Patent Application 2017-152807 (filed on Aug. 7, 2017), each of which applications is incorporated herein by reference in its entirety and to which priority is claimed.

TECHNICAL FIELD

The present invention relates to therapeutic or prophylactic agents for fatty liver disease and for obesity each comprising a specific inhibitory compound against the function of Pin1 as an active ingredient.

BACKGROUND ART

Fatty liver disease, which is also called "fatty liver," is a condition with excessive hepatic accumulation of neutral fats. Alcoholic fatty liver disease, which is caused by excessive alcohol intake, is a typical type of fatty liver disease. In addition, non-alcoholic fatty liver disease (NAFLD) has recently increased in number of cases, which is another type of fatty liver disease characterized by fat accumulation, similar to that found in cases of alcoholic fatty liver, and observed even in patients who have no history of alcohol intake sufficient to induce liver injury. Simple steatosis is a mild form of non-alcoholic fatty liver disease (NAFLD) and progresses to non-alcoholic steatohepatitis (NASH), which is a severe form of non-alcoholic fatty liver disease involving liver tissue inflammation and fibrosis. Now it is clear that NASH is a disease which eventually progresses to liver cirrhosis and liver cancer if left untreated, and the disease is thus considered clinically important.

However, no therapy for NASH has yet been established, and diet and exercise therapy is the first choice of treatment. For drug therapy, obeticholic acid (6-ethyl-chenodeoxycholic acid), which is a ligand of farnesoid X receptor (FXR), a bile acid receptor present in hepatocyte nuclei, was found to be effective for NASH (Patent Document 1), and is currently under clinical trial. NASH is a disease that eventually progresses to liver cirrhosis and liver cancer, and the number of patients with NASH is significantly increasing in developed countries. Consequently, there is strong demand for development of novel therapeutic agents for NAFLD, including NASH and a precursor thereto, namely simple steatosis.

The inventors previously found that Pin1 knockout mice were resistant to NASH development and high-fat-diet-induced obesity (Non-Patent Document 1).

Pin1 is a kind of peptidyl-prolyl cis-trans isomerase (PPIase) that catalyzes cis/trans isomerization of proline residues in proteins, and specifically acts on proline residues immediately preceded by phosphorylated serine or threonine to change the conformation of those proline residues. Accordingly, Pin1 is a molecule that couples phosphorylation of a protein to conformational change of the protein, and is considered to play an important role in intracellular signal transduction. In respect of Pin1, it is reported that Pin1 inhibitors have ability to inhibit cancer cell growth (Non-Patent Documents 2 and 3).

As compounds that inhibit Pin1, a phenylalaninol-phosphate derivative, an indole- or benzimidazole-alanine derivative, a fredericamycin A compound, a phenyl-imidazole derivative, a naphthyl-substituted amino acid derivative, a glutamate or aspartate derivative, and the like have been reported (Patent Documents 2 to 5 and Non-Patent Documents 2 to 5).

Juglone is a compound having the following structure, and is a naturally-occurring plant growth inhibitor that inhibits various enzymes, and is reported not only to have an inhibitory activity against Pin1, but also to prevent liver fibrosis and inflammation (Non-Patent Documents 6 to 8). However, the mechanism to inhibit liver fibrosis and inflammation is not fully elucidated, although several hypotheses have been proposed, since various enzymes are inhibited by Juglone (for example, Non-Patent Document 6).

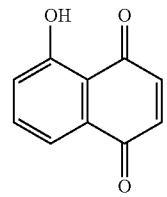 [SMILES: O=C1C=CC(=O)c2c(O)cccc21]

PRIOR ART REFERENCES

Patent Documents

Patent Document 1: WO 2005/089316
Patent Document 2: WO 2006/040646
Patent Document 3: WO 2004/087720
Patent Document 4: WO 2005/007123
Patent Document 5: WO 2002/060436

Non-Patent Documents

Non-Patent Document 1: Yusuke Nakatsu, and 20 other authors, The Journal of Biological Chemistry (J Biol Chem.), Published: Dec. 28, 2012 (Epub: Oct. 29, 2012), Vol. 287, No. 53, pp. 44526-44535.
Non-Patent Document 2: Andrew Potter, and 16 other authors, Bioorganic & Medicinal Chemistry Letters (Bioorg. Med. Chem. Lett.), Published: Nov. 15, 2010 (Epub: Sep. 17, 2010), Vol. 20, No. 22, pp. 6483-6488.
Non-Patent Document 3: Andrew Potter, and 14 other authors, Bioorganic & Medicinal Chemistry Letters (Bioorg. Med. Chem. Lett.), Published: Jan. 15, 2010 (Epub: Nov. 22, 2009), Vol. 20, No. 2, pp. 586-590.
Non-Patent Document 4: Liming Dong, and 11 other authors, Bioorganic & Medicinal Chemistry Letters (Bioorg. Med. Chem. Lett.), Published: Apr. 1, 2010 (Epub: Feb. 14, 2010), Vol. 20, No. 7, pp. 2210-2214.
Non-Patent Document 5: Hidehiko Nakagawa, and 6 other authors, Bioorganic & Medicinal Chemistry Letters (Bioorg. Med. Chem. Lett.), Published: Dec. 1, 2015 (Epub: Oct. 22, 2015), Vol. 25, pp. 5619-5624.
Non-Patent Document 6: De-Jiang Zhou, and 7 other authors, Molecular Medicine Reports (Mol Med Rep.), Published: Sep. 12, 2015 (Epub: Jun. 24, 2015), Vol. 12, No. 3, pp. 4095-4102.

Non-Patent Document 7: Jin Won Yang, and 7 other authors, Journal of Hepatology (J Hepatol.), Published: June, 2014, Vol. 60, No. 6, pp. 1235-1241.

Non-Patent Document 8: Xiaohui Peng, and 4 other authors, Biochemical and Biophysical Research Communications (Biochem Biophys Res Commun.), Published: Jul. 3, 2015 (Epub: May 9, 2015), Vol. 462, No. 3, pp. 245-250.

DISCLOSURE OF THE INVENTION

Problems to be Solved by the Invention

In view of the current conditions as described above, an object of the present invention is to develop new therapeutic agents for fatty liver disease, such as NASH and NAFLD, and for obesity.

Means for Solving the Problems

The inventors intensively studied to solve the above-described problem, and consequently found that Juglone has an inhibitory effect on liver tissue inflammation but also produces severe side effects, and that not a compound like Juglone which inhibits various enzymes, but rather a compound which has a certain structure to specifically inhibit the function of Pin1 can be used to inhibit liver tissue inflammation and fibrosis with reduced side effects and, furthermore, to reduce fat accumulation, and finally completed the present invention.

That is, the present invention provides the following first invention relating to therapeutic or prophylactic agents for fatty liver disease, and the following second invention relating to a therapeutic or prophylactic agent for obesity.

The first invention provides therapeutic or prophylactic agents for fatty liver disease, which comprises a compound represented by following Formula (I) or a pharmaceutically acceptable salt thereof as an active ingredient:

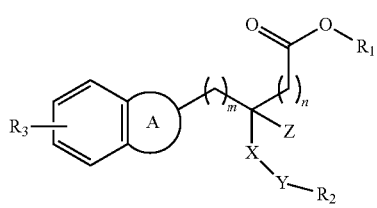

(wherein m represents an integer of 0 to 2, and n represents an integer of 0 to 1, provided that 0≤m+n≤2;

a ring A represents an optionally substituted monocyclic aromatic or heterocyclic ring;

X represents a single bond, —NH— group, —NH—CO— group, —O—CO— group, —CH$_2$—S—CH$_2$— group, —CH$_2$—S—(CH$_2$)$_2$—S— group, or —NH—R$_4$— group (R$_4$ represents a C$_{1-5}$ alkylene group or a C$_{2-5}$ alkenylene group);

Y represents a single bond, —NH— group, —CO— group, —SO$_2$— group, —O—CO— group, —CO—NR$_5$— group (R$_5$ represents a hydrogen atom or an optionally substituted C$_{1-5}$ alkyl group), —O—R$_6$— group (R$_6$ represents an optionally substituted C$_{1-5}$ alkylene group or an optionally substituted C$_{2-5}$ alkenylene group), —NR$_5$—R$_6$— group, —S—R$_6$— group, —CO—R$_6$— group, —SO$_2$—R$_6$— group, —NR—CO—R$_6$— group, —R$_6$—NR$_5$—CO— group, an optionally substituted C$_{1-6}$ alkylene group, or an optionally substituted C$_{2-6}$ alkenylene group;

Z represents a hydrogen atom, an optionally substituted amino group, or an optionally substituted amine, provided that X and Z forms a ring when Z represents an optionally substituted amine;

R$_1$ represents a hydrogen atom, an optionally substituted hydrocarbon group, an optionally substituted heterocyclic group, or an optionally substituted amino group;

R$_2$ represents an optionally substituted aryl group, an optionally substituted heterocyclic group, an optionally substituted cycloalkyl group, or a group represented by the following Formula (II):

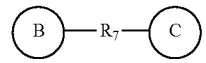

(II)

(wherein rings B and C independently represent an optionally substituted aryl group, an optionally substituted heterocyclic group, or an optionally substituted cycloalkyl group, and R$_7$ represents a single bond, —O— group, —CO— group, —NH— group, —SO$_2$— group, —CO—NH— group, an optionally substituted C$_{1-3}$ alkylene group, an optionally substituted C$_{2-3}$ alkenylene group, —S—R$_8$— group (R$_8$ represents an optionally substituted C$_{1-2}$ alkylene group), —CO—R$_8$— group, —O—R$_8$— group, or —SO$_2$—R— group, and Y is attached to any of the ring B, ring C, and R$_7$); and R$_3$ represents 0 to 4 identical or different substituents).

For the therapeutic or prophylactic agents for fatty liver disease according to the first invention, the fatty liver disease is preferably non-alcoholic steatohepatitis.

In any aforementioned therapeutic or prophylactic agent for fatty liver disease, m and n are preferably 1 and 0, respectively.

In any aforementioned therapeutic or prophylactic agent for fatty liver disease, X preferably represents an —NH—CO— group or a —O—CO— group.

In any aforementioned therapeutic or prophylactic agent for fatty liver disease, the ring A preferably represents a benzene ring.

In any aforementioned therapeutic or prophylactic agent for fatty liver disease, the R$_2$ preferably represents an optionally substituted polycyclic aryl group or an optionally substituted polycyclic heterocyclic group.

In any aforementioned therapeutic or prophylactic agent for fatty liver disease, Z preferably represents a hydrogen atom.

In any aforementioned therapeutic or prophylactic agent for fatty liver disease, Y preferably represents a single bond, —CH$_2$— group, or —CH$_2$—O— group. In any aforementioned therapeutic or prophylactic agent for fatty liver disease, the R$_1$ preferably represents a hydrogen atom.

Any aforementioned therapeutic or prophylactic agent for fatty liver disease may further comprise active ingredients in at least one or more drugs selected from the group of other therapeutic or prophylactic agents for fatty liver disease.

Moreover, any aforementioned therapeutic or prophylactic agent for fatty liver disease may be used in combination with at least one or more drugs selected from the group of other therapeutic or prophylactic agents for fatty liver disease.

The first invention provides any aforementioned compound or a pharmaceutically acceptable salt thereof for use as a therapeutic or prophylactic agent for fatty liver disease.

The first invention also provides use of any aforementioned compound or a pharmaceutically acceptable salt thereof for the manufacture of a medicament for the treatment or prevention of fatty liver disease.

Moreover, the first invention also provides a method of treating or preventing fatty liver disease by administering any aforementioned compound or a pharmaceutically acceptable salt thereof to a patient.

The second invention provides therapeutic or prophylactic agents for obesity, which comprises a compound represented by following Formula (I) or a pharmaceutically acceptable salt thereof as an active ingredient:

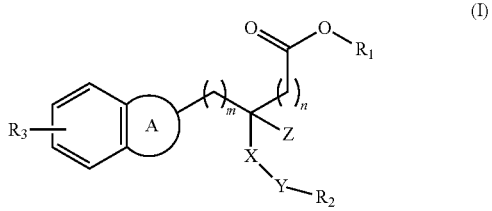

(I)

(wherein m represents an integer of 0 to 2, and n represents an integer of 0 to 1, provided that $0 \leq m+n \leq 2$;

a ring A represents an optionally substituted monocyclic aromatic or heterocyclic ring;

X represents a single bond, —NH— group, —NH—CO— group, —O—CO— group, —CH$_2$—S—CH$_2$— group, —CH$_2$—S—(CH$_2$)$_2$—S— group, or —NH—R$_4$— group (R$_4$ represents a C$_{1-5}$ alkylene group or a C$_{2-5}$ alkenylene group);

Y represents a single bond, —NH— group, —CO— group, —SO$_2$— group, —O—CO— group, —CO—NR$_5$— group (R$_5$ represents a hydrogen atom or an optionally substituted C$_{1-5}$ alkyl group), —O—R$_6$— group (R$_6$ represents an optionally substituted C$_{1-5}$ alkylene group or an optionally substituted C$_2$— alkenylene group), —NR$_5$—R$_6$— group, —S—R$_6$— group, —CO—R$_6$— group, —SO$_2$—R$_6$— group, —NR—CO—R$_6$— group, —R$_6$—NR$_5$—CO— group, an optionally substituted C$_{1-6}$ alkylene group, or an optionally substituted C$_{2-6}$ alkenylene group;

Z represents a hydrogen atom, an optionally substituted amino group, or an optionally substituted amine, provided that X and Z forms a ring when Z represents an optionally substituted amine;

R$_1$ represents a hydrogen atom, an optionally substituted hydrocarbon group, an optionally substituted heterocyclic group, or an optionally substituted amino group;

R$_2$ represents an optionally substituted aryl group, an optionally substituted heterocyclic group, an optionally substituted cycloalkyl group, or a group represented by the following Formula (II):

(II)

(wherein rings B and C independently represent an optionally substituted aryl group, an optionally substituted heterocyclic group, or an optionally substituted cycloalkyl group, and R$_7$ represents a single bond, —O— group, —CO— group, —NH— group, —SO$_2$— group, —CO—NH— group, an optionally substituted C$_{1-3}$ alkylene group, an optionally substituted C$_{2-3}$ alkenylene group, —S—R$_8$— group (R$_8$ represents an optionally substituted C$_{1-2}$ alkylene group), —CO—R$_8$— group, —O—R$_8$— group, or —SO$_2$—R— group, and Y is attached to any of the ring B, ring C, and R$_7$); and R$_3$ represents 0 to 4 identical or different substituents).

In the therapeutic or prophylactic agents for obesity according to the second invention, m and n are preferably 1 and 0, respectively.

In any aforementioned therapeutic or prophylactic agent for obesity, X preferably represents an —NH—CO— group or a —O—CO— group.

In any aforementioned therapeutic or prophylactic agent for obesity, the ring A preferably represents a benzene ring.

In any aforementioned therapeutic or prophylactic agent for obesity, the R$_2$ preferably represents an optionally substituted polycyclic aryl group or an optionally substituted polycyclic heterocyclic group.

In any aforementioned therapeutic or prophylactic agent for obesity, Z preferably represents a hydrogen atom.

In any aforementioned therapeutic or prophylactic agent for obesity, Y preferably represents a single bond, —CH$_2$— group, or —CH$_2$—O— group.

In any aforementioned therapeutic or prophylactic agent for obesity, the R$_1$ preferably represents a hydrogen atom.

Any aforementioned therapeutic or prophylactic agent for obesity may further comprise active ingredients in at least one or more drugs selected from the group of other therapeutic or prophylactic agents for obesity.

Moreover, any aforementioned therapeutic or prophylactic agent for obesity may be used in combination with at least one or more drugs selected from the group of other therapeutic or prophylactic agents for obesity.

The second invention provides any aforementioned compound or a pharmaceutically acceptable salt thereof for use as a therapeutic or prophylactic agent for obesity.

The second invention also provides use of any aforementioned compound or a pharmaceutically acceptable salt thereof for the manufacture of a medicament for the treatment or prevention of obesity.

Moreover, the second invention also provides a method of treating or preventing obesity by administering any aforementioned compound or a pharmaceutically acceptable salt thereof to a patient.

Effect of the Invention

Therapeutic or prophylactic agents for fatty liver disease according to the first invention have effects to inhibit liver inflammation and fibrosis and to reduce accumulation of fat in the liver and thereby to treat or prevent fatty liver disease. Therapeutic or prophylactic agents for obesity according to the second invention have an effect to reduce accumulation of body fat and thereby to treat or prevent obesity.

BRIEF DESCRIPTION OF THE DRAWINGS

FIG. 1 (A) is a graph depicting the result of measurement of mouse liver weight, and FIG. 1 (B) is a graph depicting the result of measurement of blood ALT (GPT) concentration in mice, and FIG. 1 (C) is a graph depicting the result of measurement of fasting blood glucose concentration in mice. In each of FIGS. 1 (A) to (C), graph bars represent the measurement results in control mice, NASH mice, NASH mice treated by intraperitoneal administration of H-163, NASH mice treated by oral administration of H-163, NASH mice treated by intraperitoneal administration of H-144, NASH mice treated by oral administration of H-144, NASH mice treated by intraperitoneal administration of Juglone, and NASH mice treated by oral administration of Juglone, from left to right.

FIG. 2 (A) is a photograph depicting the result of observation of liver tissue from control mice given a normal diet, and FIG. 2 (B) is a photograph depicting the result of observation of liver tissue from NASH mice given a HFDT, and FIG. 2 (C) is a photograph depicting the result of observation of liver tissue from NASH mice given a HFDT and H-163.

FIG. 3 (A) is a photograph depicting the result of observation of liver tissue from control mice given a normal diet, and FIG. 3 (B) is a photograph depicting the result of observation of liver tissue from NASH mice given a MCDD, and FIG. 3 (C) is a photograph depicting the result of observation of liver tissue from NASH mice given a MCDD and H-163, and FIG. 3 (D) is a photograph depicting the result of observation of liver tissue from NASH mice given a MCDD and H-31.

FIG. 4 (A) is a graph depicting the result of measurement of Collagen 1a1 mRNA expression level, and FIG. 4 (B) is a graph depicting the result of measurement of Collagen 1a2 mRNA expression level, and FIG. 4 (C) is a graph depicting the result of measurement of SMA mRNA expression level. In each graph, graph bars represent the result of measurement of each mRNA expression level in control mice given a normal diet, NASH mice given a MCDD, NASH mice given a MCDD and H-31, and NASH mice given a MCDD and H-163, from left to right.

DESCRIPTION OF EMBODIMENTS

Figure 1:
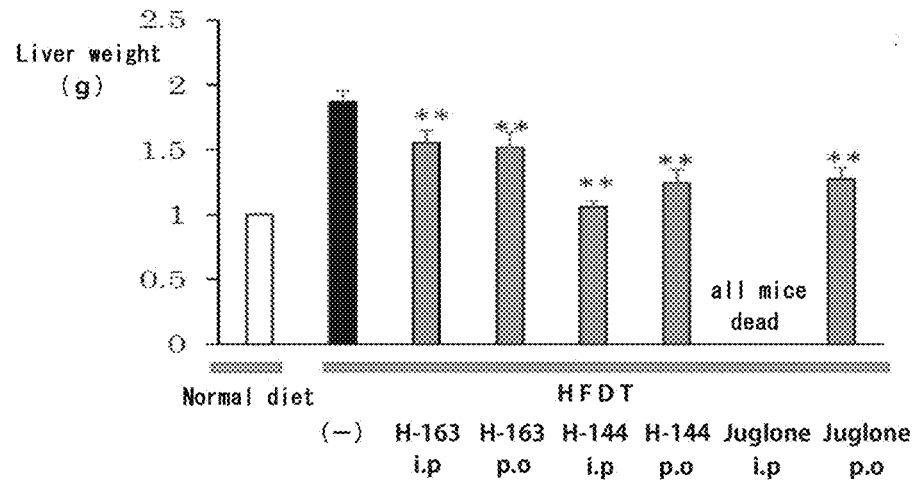
FIG. 1 shows graphs depicting results of measurements of liver weight, blood ALT (GPT) concentration, and fasting blood glucose concentration in mice in a NASH treatment study.
Figure 1:
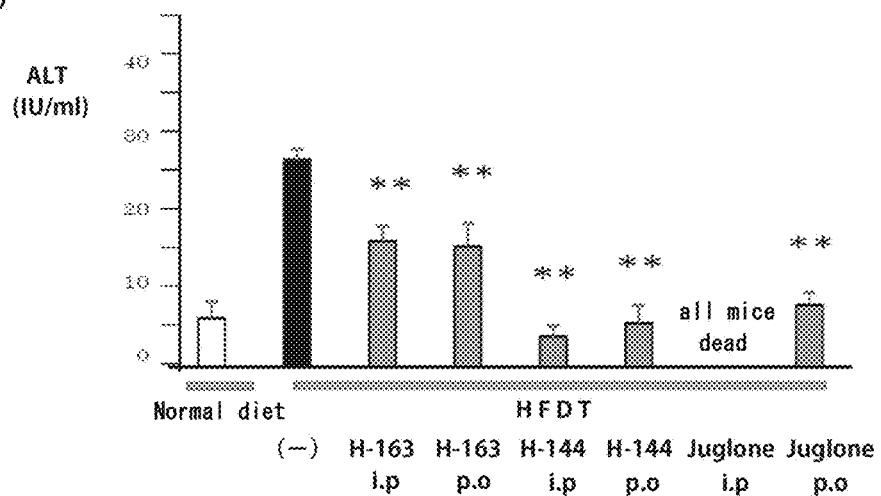
Figure 1:
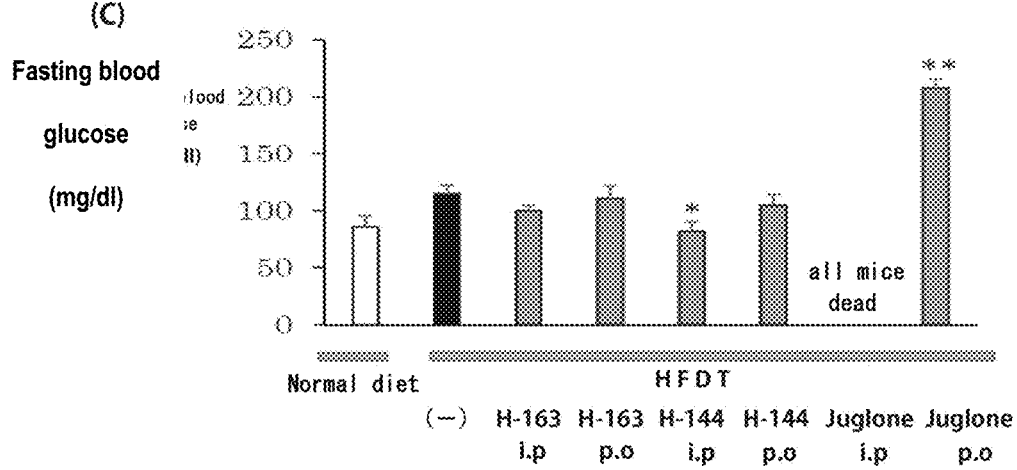

1. Therapeutic or Prophylactic Agents for Fatty Liver Disease 1-1. Chemical Structure of an Active Ingredient Compounds that are used as active ingredients in therapeutic or prophylactic agents for fatty liver disease according to the present invention have a chemical structure represented by the following Formula (I) and an inhibitory activity against the function of Pin1.

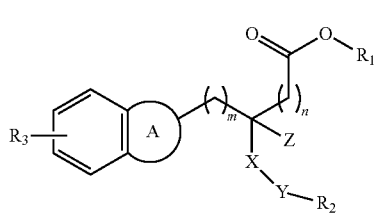
(I)

In the Formula (I), m represents an integer of 0 to 2, and n represents an integer of 0 to 1, provided that m and n are integers that satisfy the following relation: $0 \leq m+n \leq 2$. That is, there are five combinations of (m, n): (0, 0), (0, 1), (1, 0), (1, 1), and (2, 0).

The compounds used as active ingredients in the present invention can have any of five chemical structures represented by the following Formula (III) to (VII) and based on the five combinations of (m, n).

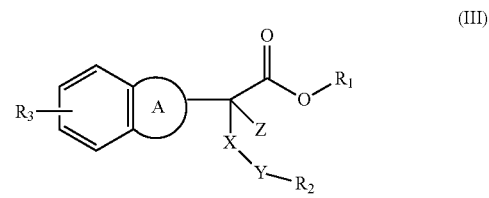
(III)

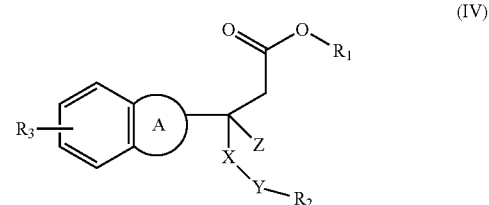
(IV)

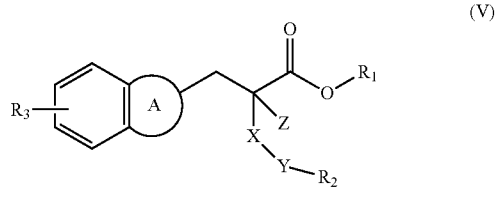
(V)

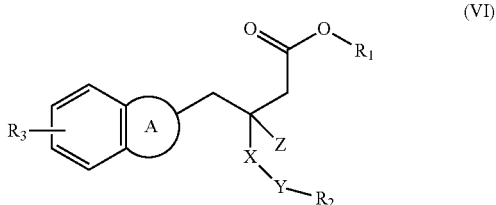
(VI)

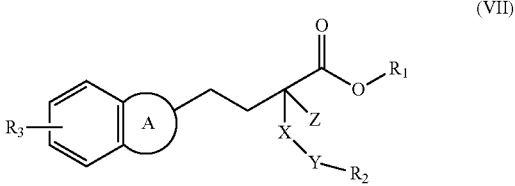
(VII)

The Formula (III) represents a variation of the Formula (I), where m=1 and n=0.

The Formula (IV) represents a variation of the Formula (I), where m=0 and n=1.

The Formula (V) represents a variation of the Formula (I), where in 1 and n=0.

The Formula (VI) represents a variation of the Formula (I), where m=1 and n=1.

The Formula (VII) represents a variation of the Formula (I), where m=2 and n=0.

The compounds used as active ingredients in the present invention are preferably represented by the Formula (V), where m=1 and n=0.

In the above Formula (I), the ring A represents an optionally substituted monocyclic aromatic ring or an optionally substituted monocyclic heterocyclic ring.

In the present invention, the "monocyclic aromatic ring" refers to an unsaturated organic compound containing one ring composed of carbon and hydrogen atoms, and can be, but is not limited to, for example, benzene ring, cyclopentadiene ring, or the like.

In the present invention, the "monocyclic heterocyclic ring" refers to an unsaturated organic compound containing one ring composed of atoms of carbon, hydrogen, and some other elements, and can be, but is not limited to, pyrrole ring, imidazole ring, pyrazole ring, furan ring, thiophene ring, isothiazole ring, isoxazole ring, pyridine ring, pyrazine ring, pyrimidine ring, pyridazine ring, pyran ring, pyrroline ring, or the like.

The ring A is conjugated with a neighboring benzene ring to form a condensed ring, whereby a group containing a bicyclic condensed ring is formed. Examples of the group containing a bicyclic condensed ring can include, but are not limited to, naphthyl group, indenyl group, indolyl group, benzimidazolyl group, isoindolyl group, 3H-indolyl group, 1H-indazolyl group, isobenzofuranyl group, quinolyl group, isoquinolyl group, phthalazinyl group, quinoxalinyl group, quinazolinyl group, cinnolinyl group, and chromenyl group, which are each optionally substituted.

Among those groups, an optionally substituted naphthyl group, an optionally substituted indolyl group, or an optionally substituted benzimidazolyl group is preferred as the group containing a bicyclic condensed ring. A substituted naphthyl group is more preferred as the group containing a bicyclic condensed ring, and the ring A in this case is benzene ring.

With regard to structure, the compounds used as active ingredients in the present invention are roughly divided into two parts, composed of a cyclic moiety consisting of a group containing a bicyclic condensed ring, which contains a benzene ring and a ring A, and a chain moiety attached to the cyclic moiety.

In cases where an optionally substituted naphthyl group is used as the group containing a bicyclic condensed ring (the cyclic moiety), the chain moiety can be attached to position 1 or 2 of the naphthyl group. Preferably, the chain moiety should be attached to position 2 of the naphthyl group.

In cases where an optionally substituted indolyl group is used as the group containing a bicyclic condensed ring (the cyclic moiety), the chain moiety can be attached to position 1, 2, or 3 of the indolyl group. Preferably, the chain moiety should be attached to position 2 or 3 of the indolyl group.

In cases where an optionally substituted benzimidazolyl group is used as the group containing a bicyclic condensed ring (the cyclic moiety), the chain moiety can be attached to position 1 or 2 of the benzimidazolyl group. Preferably, the chain moiety should be attached to position 2 of the benzindolyl group.

The chemical structure of the group containing a bicyclic condensed ring (the cyclic moiety) can be specifically illustrated by, but not limited to, those of the following groups.

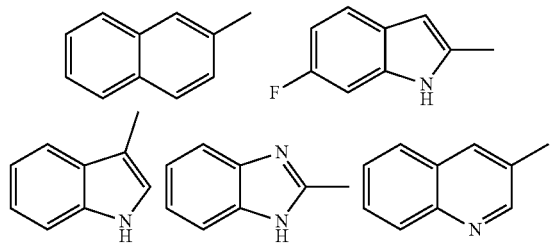

In the above Formula (I), X represents a single bond, —NH— group, —NH—CO— group, —O—CO— group, —CH$_2$—S—CH$_2$— group, —CH$_2$—S—(CH$_2$)$_2$—S— group, or —NH—R$_4$— group (R$_4$ represents a C$_{1-5}$ alkylene group or a C$_{2-5}$ alkenylene group).

These groups are all divalent groups and may be oriented in either direction to get attached to Y. For example, in cases where X represents —NH—CO—, Y may be attached to the CO— or the —NH.

In this respect, examples of the "C$_{1-5}$ alkylene group" in the present invention include, but are not limited to, linear or branched alkylene groups, such as methylene group, ethylene group, trimethylene group, 2-methyltrimethylene group, and pentamethylene group.

Moreover, examples of the "C$_{2-5}$ alkenylene group" in the present invention include, but are not limited to, linear or branched alkenylene groups containing two to five carbon atoms and having one to three double bonds, such as vinylene group, 1-propenylene group, 1-methyl-1-propenylene group, 2-methyl-1-propenylene group, 2-butenylene group, 2-pentenylene group, 1,3-butadienylene group, and 3-dimethyl-1-propenylene group.

In the above Formula (I), Y represents a single bond, —NH— group, —CO— group, —SO$_2$— group, —O— CO— group, —CO—NR$_5$— group (R$_5$ represents a hydrogen atom or an optionally substituted C$_{1-5}$ alkyl group), —O—R$_6$— group (R$_6$ represents an optionally substituted C$_{1-5}$ alkylene group or an optionally substituted C$_{2-5}$ alkenylene group), —NR$_5$—R$_6$— group, —S—R$_6$— group, —CO—R$_6$— group, —SO$_2$—R$_6$— group, —NR—CO— R$_6$— group, —R$_6$—NR—CO— group, an optionally substituted C$_{1-6}$ alkylene group, or an optionally substituted C$_{2-6}$ alkenylene group.

These groups are all divalent groups and may be oriented in either direction to get attached to R$_2$. For example, in cases where Y represents a —O—CO— group, R$_2$ may be attached to either the CO— or the —O.

Examples of the "C$_{1-6}$ alkylene group" in the present invention include, but are not limited to, linear or branched alkylene groups, such as methylene group, ethylene group, trimethylene group, 2-methyltrimethylene group, pentamethylene group, hexamethylene group, and 3-methylpentamethylene group.

Moreover, examples of the "C$_{2-6}$ alkenylene group" in the present invention include, but are not limited to, linear or branched alkenylene groups containing two to six carbon atoms and having one to three double bonds, such as vinylene group, 1-propenylene group, 1-methyl-1-propenylene group, 2-methyl-1-propenylene group, 2-butenylene group, 2-pentenylene group, 1,3-butadienylene group, 3-dimethyl-1-propenylene group, 1,4-hexadienylene group, and 4-methyl-3-pentenylene group.

In the above Formula (I), R$_1$ represents a hydrogen atom, an optionally substituted hydrocarbon group, an optionally substituted heterocyclic group, or an optionally substituted amino group.

In cases where R$_1$ represents a hydrogen atom to form a carboxyl group, the compounds used as active ingredients in the present invention have an inhibitory activity against the function of Pin1. Thus, R$_1$ preferably represents a hydrogen atom.

However, in cases where R$_1$ represents an optionally substituted hydrocarbon group, an optionally substituted heterocyclic group, or an optionally substituted amino group, the R$_1$ moiety in the compound represented by the Formula (I) is attached via an ester bond, and the ester bond can be hydrolyzed to form a carboxyl group. Thus, even if $R_1$ is an optionally substituted hydrocarbon group, an optionally substituted heterocyclic group, or an optionally substituted amino group, the compounds used as active ingredients in the present invention can be used as prodrugs.

In the present invention, the "hydrocarbon group" used for, for example, $R_1$ in the Formula (I) means a group derived from a compound composed of carbon and hydrogen atoms. Examples of the hydrocarbon group can include, but are not limited to, aliphatic hydrocarbon, monocyclic saturated hydrocarbon, and aromatic hydrocarbon groups, and preferably contain 1 to 16 carbon atoms. Specific examples of the hydrocarbon group include, but are not limited to, alkyl groups, alkenyl groups, alkynyl groups, cycloalkyl groups, aryl groups, and aralkyl groups.

In this respect, examples of "alkyl group" include methyl group, ethyl group, propyl group, isopropyl group, butyl group, isobutyl group, sec-butyl group, tert-butyl group, pentyl group, and hexyl group. Examples of "alkenyl group" include vinyl group, 1-propenyl group, allyl group, isopropenyl group, butenyl group, and isobutenyl group. Examples of "alkynyl group" include ethynyl group, propargyl group, and 1-propynyl group. Examples of "cycloalkyl group" include cyclopropyl group, cyclobutyl group, cyclopentyl group, and cyclohexyl group. Examples of "aryl group" include phenyl group, indenyl group, naphthyl group, fluorenyl group, anthryl group, biphenylenyl group, phenanthrenyl group, as-indacenyl group, s-indacenyl group, acenaphthylenyl group, phenalenyl group, fluoranthenyl group, pyrenyl group, naphthacenyl group, and hexacenyl group. Examples of "aralkyl group" include benzyl group, styryl group, and phenethyl group.

In the present invention, the "heterocyclic group" used for, for example, $R_1$ in the Formula (I) refers to a group derived from a cyclic compound composed of atoms of carbon and some other elements. As the "heterocyclic group," an aromatic heterocyclic group is preferably used.

The "heterocyclic group" in the present invention can be, but is not limited to, for example, any of 5- to 14-membered monocyclic to pentacyclic heterocyclic groups each having carbon atoms and further having one to four heteroatoms of one or two elements selected from nitrogen, oxygen, and sulfur. Specific examples of the heterocyclic group can include, but are not limited to, 5-membered cyclic groups each having carbon atoms and further having one to four heteroatoms selected from oxygen, sulfur, and nitrogen, such as 2- or 3-thienyl group, 2- or 3-furyl group, 1-, 2- or 3-pyrrolyl group, 1-, 2- or 3-pyrrolidinyl group, 2-, 4- or 5-oxazolyl group, 3-, 4- or 5-isooxazolyl group, 2-, 4- or 5-thiazolyl group, 3-, 4- or 5-isothiazolyl group, 3-, 4- or 5-pyrazolyl group, 2-, 3- or 4-pyrazolidinyl group, 2-, 4- or 5-imidazolyl group, 1,2,3-triazolyl group, 1,2,4-triazolyl group, and 1H- or 2H-tetrazolyl group. Moreover, specific examples of the heterocyclic group can include 6-membered cyclic groups each having carbon atoms and further having one to four heteroatoms selected from oxygen, sulfur, and nitrogen, such as 2-, 3- or 4-pyridyl group, N-oxide-2-, 3- or 4-pyridyl group, 2-, 4- or 5-pyrimidinyl group, N-oxide-2-, 4- or 5-pyrimidinyl group, thiomorpholinyl group, morpholinyl group, piperidino group, 2-, 3- or 4-piperidyl group, thiopyranyl group, 1,4-oxazinyl group, 1,4-thiazinyl group, 1,3-thiazinyl group, piperazinyl group, triazinyl group, 3- or 4-pyridazinyl group, pyrazinyl group, and N-oxide-3- or 4-pyridazinyl group. Moreover, specific examples of the heterocyclic group can include bicyclic to tetracyclic condensed ring groups each having carbon atoms and further having one to four heteroatoms selected from oxygen, sulfur, and nitrogen, such as indolyl group, benzofuryl group, benzothiazolyl group, benzoxazolyl group, xanthenyl group, benzimidazolyl group, quinolyl group, isoquinolyl group, phthalazinyl group, quinazolinyl group, quinoxalinyl group, indolizinyl group, quinolizinyl group, 1,8-naphthyridinyl group, dibenzofuranyl group, carbazolyl group, acridinyl group, phenanthridinyl group, perimidinyl group, phenazinyl group, chromanyl group, phenothiazinyl group, phenoxazinyl group, and 7H-pirazino[2,3-c]carbazolyl group.

In the above Formula (I), $R_2$ represents an optionally substituted aryl group, an optionally substituted heterocyclic group, an optionally substituted cycloalkyl group, or a group represented by the Formula (II).

In this respect, examples of the "aryl group" in the present invention can include, but are not limited to, phenyl group, indenyl group, naphthyl group, fluorenyl group, anthryl group, biphenylenyl group, phenanthrenyl group, as-indacenyl group, s-indacenyl group, acenaphthylenyl group, phenalenyl group, fluoranthenyl group, pyrenyl group, naphthacenyl group, and hexacenyl group.

Moreover, examples of the "cycloalkyl group" in the present invention can include, but are not limited to, cyclopropyl group, cyclobutyl group, cyclopentyl group, cyclohexyl group, cycloheptyl group, and cyclooctyl group.

The $R_2$ in the Formula (I) can be a group represented by the Formula (II), and the structure of the Formula (II) is illustrated below.

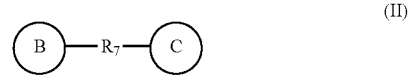

(II)

In the Formula (II), the rings B and C independently represent an optionally substituted aryl group, an optionally substituted heterocyclic group, or an optionally substituted cycloalkyl group, and $R_7$ represents a single bond, —O— group, —CO— group, —NH— group, —SO$_2$— group, —CO—NH— group, an optionally substituted $C_{1-3}$ alkylene group, an optionally substituted $C_{2-3}$ alkenylene group, —S—$R_8$— group ($R_8$ represents an optionally substituted $C_{1-2}$ alkylene group), —CO—$R_8$— group, —O—$R_8$— group, or —SO$_2$—$R_8$— group.

In this respect, the "$C_{1-2}$ alkylene group" refers to methylene group or ethylene group, and examples of the "$C_{1-3}$ alkylene group" can include trimethylene group, in addition to the above-described alkylene groups.

Moreover, examples of the "$C_{2-3}$ alkenylene group" include vinylene group and 1-propenylene group.

In cases where $R_2$ in the above Formula (I) is a group represented by the Formula (II), Y is attached to any of the ring B, ring C, and $R_7$.

The structure where Y is attached to the ring B is represented by the following Formula (VIII), and the structure where Y is attached to the ring C is represented by the following Formula (IX), and the structure where Y is attached to $R_7$ is represented by the following Formula (X).

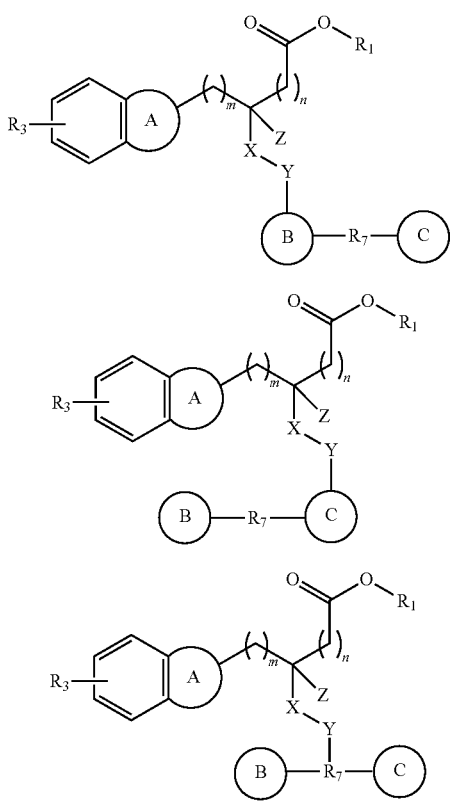

R$_2$ in the above Formula (I) preferably represents an optionally substituted polycyclic aryl group or an optionally substituted polycyclic heterocyclic group to form a compound with high activity.

In the above Formula (I), R$_3$ represents identical or different substituents. The "substituent" in the present invention is a halogen (such as, for example, fluorine, chlorine, bromine, or iodine), an alkyl group (for example, a C$_{1-6}$ alkyl group, such as methyl group, ethyl group, propyl group, isopropyl group, butyl group, isobutyl group, sec-butyl group, tert-butyl group, pentyl group, or hexyl group), a cycloalkyl group (for example, a C$_{3-6}$ cycloalkyl group, such as cyclopropyl group, cyclobutyl group, cyclopentyl group, or cyclohexyl group), an alkynyl group (for example, a C$_{2-6}$ alkynyl group, such as ethynyl group, 1-propynyl group, or propargyl group), an alkenyl group (for example, a C$_{2-6}$ alkenyl group, such as vinyl group, allyl group, isopropenyl group, butenyl group, or isobutenyl group), an aralkyl group (for example, a C$_{7-11}$ aralkyl group, such as benzyl group, α-methylbenzyl group, or phenethyl group), an aryl group (for example, a C$_{6-10}$ aryl group, such as phenyl group or naphthyl group; preferably phenyl group), an alkoxy group (for example, a C$_{1-6}$ alkoxy group, such as methoxy group, ethoxy group, propoxy group, isopropoxy group, butoxy group, isobutoxy group, sec-butoxy group, or tert-butoxy), an aryloxy group (for example, a C$_{6-10}$ aryloxy group, such as phenoxy), an alkanoyl group (for example, a C$_{1-6}$ alkyl-carbonyl group, such as formyl group, acetyl group, propionyl group, butyryl group, or isobutyryl group), an arylcarbonyl group (for example, a C$_{6-10}$ aryl-carbonyl group, such as benzoyl group or naphthoyl group), an alkanoyloxy group (for example, a C$_{1-6}$ alkyl-carbonyloxy group, such as formyloxy group, acetyloxy group, propionyloxy group, butyryloxy group, or isobutyryloxy group), an arylcarbonyloxy group (for example, a C$_{6-10}$ aryl-carbonyloxy group, such as benzoyloxy group or naphthoyloxy group), carboxyl group, an alkoxycarbonyl group (for example, a C$_{1-6}$ alkoxy-carbonyl group, such as methoxycarbonyl group, ethoxycarbonyl group, propoxycarbonyl group, isopropoxycarbonyl group, butoxycarbonyl group, isobutoxycarbonyl group, or tert-butoxycarbonyl), an aralkyloxycarbonyl group (for example, a C$_{7-11}$ aralkyloxycarbonyl group, such as benzyloxycarbonyl group), carbamoyl group, a halogenated alkyl group (for example, a mono-, di-, or tri-halogenated —C$_{1-4}$ alkyl group, such as chloromethyl group, dichloromethyl group, trifluoromethyl group, or 2,2,2-trifluoroethyl group), oxo group, amidino group, imino group, amino group, an alkylamino group (for example, a mono-C$_{1-4}$ alkylamino group, such as methylamino group, ethylamino group, propylamino group, isopropylamino group, or butylamino group), a dialkylamino group (for example, a di-C$_{1-4}$ alkylamino group, such as dimethylamino group, diethylamino group, dipropylamino group, diisopropylamino group, dibutylamino group, or methylethylamino group), an alkoxycarbonylamino group (for example, a C$_{1-6}$ alkoxycarbonylamino group, such as methoxycarbonylamino group, isoproxycarbonylamino group, or tert-butoxycarbonylamino group), a cyclic amino group (a 3- to 6-membered cyclic amino group containing carbon atoms and one nitrogen atom and further containing one to three heteroatoms selected from oxygen, sulfur, and nitrogen; such as, for example, aziridinyl group, azetidinyl group, pyrrolidinyl group, pyrrolinyl group, pyrrolyl group, imidazolyl group, pyrazolyl group, imidazolidinyl group, piperidyl group, morpholinyl group, dihydropyridyl group, pyridyl group, N-methylpiperazinyl group, or N-ethylpiperazinyl group), alkylenedioxy group (for example, a C$_{1-3}$ alkylenedioxy group, such as methylenedioxy group or ethylenedioxy group), hydroxy group, cyano group, mercapto group, sulfo group, sulfino group, phosphono group, sulfamoyl group, a monoalkylsulfamoyl group (for example, a mono-C$_{1-6}$ alkylsulfamoyl group, such as N-methylsulfamoyl, N-ethylsulfamoyl, N-propylsulfamoyl, N-isopropylsulfamoyl, or N-butylsulfamoyl), a dialkylsulfamoyl group (for example, a di-C$_{1-6}$ alkylsulfamoyl group, such as N,N-dimethylsulfamoyl group, N,N-diethylsulfamoyl group, N,N-dipropylsulfamoyl group, or N,N-dibutylsulfamoyl group), an alkylthio group (for example, a C$_{1-6}$ alkylthio group, such as methylthio group, ethylthio group, propylthio group, isopropylthio group, butylthio group, sec-butylthio group, or tert-butylthio group), an arylthio group (for example, a C$_{6-10}$ arylthio group, such as phenylthio group or naphthylthio group), an alkylsulfinyl group (for example, a C$_{1-6}$ alkylsulfinyl group, such as methylsulfinyl group, ethylsulfinyl group, propylsulfinyl group, or butylsulfinyl group), an alkylsulfonyl group (for example, a C$_{1-6}$ alkylsulfonyl group, such as methylsulfonyl group, ethylsulfonyl group, propylsulfonyl group, or butylsulfonyl group), or an arylsulfonyl group (for example, a C$_{6-10}$ arylsulfonyl group, such as phenylsulfonyl group or naphthylsulfonyl group).

Among those substituents, low-molecular-weight substituents containing 1 to 10 atoms are preferred as the substituent. Examples of such a substituent that can be used include, but are not limited to, halogens, methyl group, ethyl group, vinyl group, methoxy group, ethoxy group, acetyl group, carboxyl group, methoxycarbonyl group, chloromethyl group, amino group, methylamino group, hydroxy group, sulfo group, and methylthio group.

In the present invention, the phrase "optionally substituted" means that a substituent as described above is present or absent. In cases where a moiety is substituted, two or more substituents may be present within the moiety, and the substituents may be identical to or different from each other. In cases where a compound according to the present invention is "optionally substituted," the number of substituents within the compound is preferably from 0 to 3.

In the above Formula (I), Z represents a hydrogen atom, an optionally substituted amino group, or an optionally substituted amine.

In this respect, the "optionally substituted amino group" in the present invention refers to a primary amino group, a secondary amino group, or a tertiary amino group. The primary amino group refers to —$NH_2$ group. The secondary amino group is an amino group having one substituent. Examples of the secondary amino group can include, but are not limited to, alkylamino groups, arylamino groups, and alkoxycarbonylamino groups. In addition, the tertiary amino group refers to an amino group having two identical or different substituents. Examples of the tertiary amino group can include, but are not limited to, dialkylamino groups and diarylamino groups.

In cases where Z represents an optionally substituted amine, X and Z together form a ring. The phrase "together form a ring" refers to ring formation involving attachment of Z, which is —NH—, —N═, or —NR— (R represents a substituent), to any atom in X.

The ring formed by X and Z can be, but is not limited to, for example, a dihydrothiazole ring formed by attachment of Z, which represents —N═, to a carbon atom in X, which is —$CH_2$—S—$CH_2$— group or —$CH_2$—S—$(CH_2)_2$—S— group, through a double bond. Additionally, the ring can be a piperidine ring formed by attachment of Z, which is —NH—, to a carbon atom in X, which is tetramethylene group.

In the above Formula (I), a dihydrothiazole ring formed by X and Z can be represented by the following Formula (XI) when X represents —$CH_2$—S—$CH_2$— group and Z represents —N═:

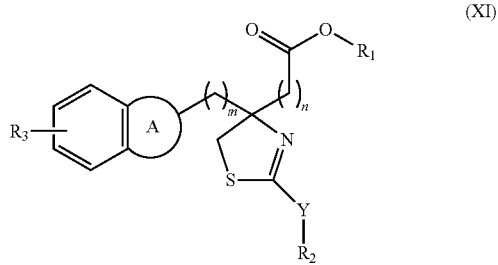

(XI)

(wherein m, n, A, Y, $R_1$, $R_2$, and $R_3$ are the same as defined above).

Synthesis of many different types of compounds represented by the above Formula (XI) is disclosed in Patent Document 2 (WO 2006/040646), and those compounds are confirmed to have an inhibitory activity against Pin1. The chemical structures of some of the compounds are specifically illustrated as follows.

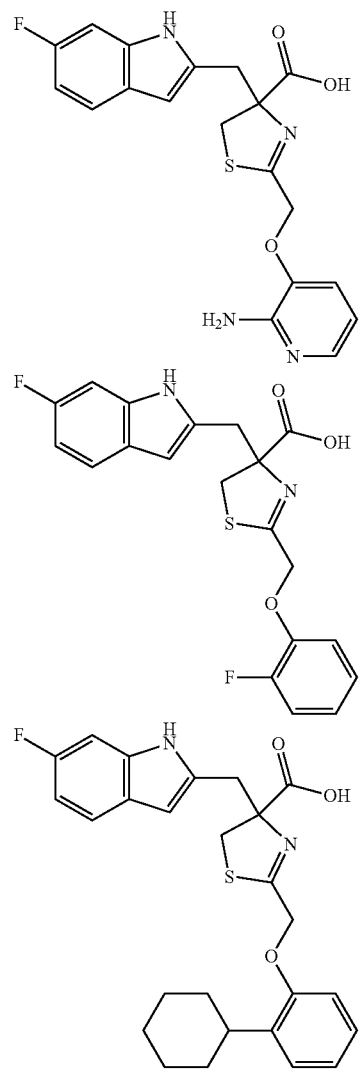

These compounds are all compounds represented by the Formula (XI), where Y represents —O—$CH_2$— group (a —O—$R_6$— group).

In the above Formula (I), a dihydrothiazole ring formed by X and Z can be represented by the following Formula (XII) when X represents -$CH_2$—S—$(CH_2)_2$—S— group and Z represents —N═group:

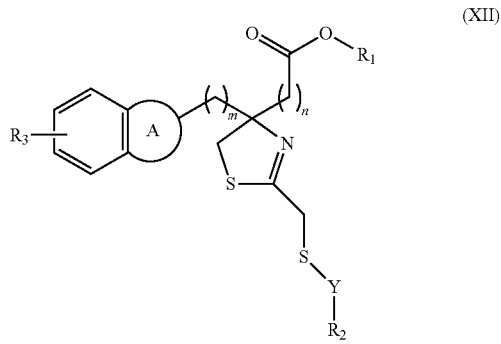

(XII)

(wherein m, n, A, Y, $R_1$, $R_2$, and $R_3$ are the same as defined above).

Synthesis of many different types of compounds represented by the above Formula (XII) is disclosed in Patent Document 2 (WO 2006/040646), and those compounds are confirmed to have an inhibitory activity against Pin1. The chemical structures of some of the compounds are specifically illustrated as follows.

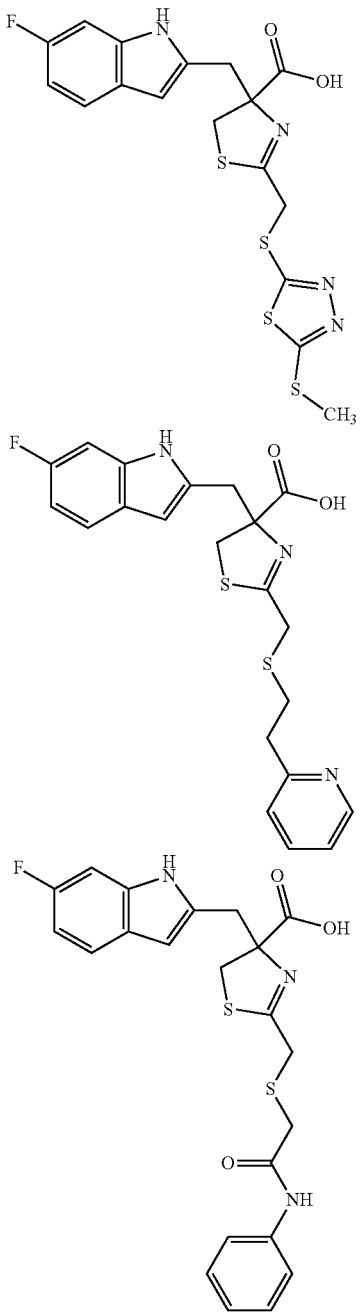

These compounds are compounds represented by the Formula (XII), where Y represents a single bond, a —$CH_2$—$CH_2$— group (an alkylene group), and a —$CH_2$—CO—NH— group (a —$NR_5$—CO—$R_6$— group).

In compounds represented by the above Formula (I), X may represent an —NH—CO— group. Preferably, starting materials for synthesis of the compounds, such as amino acid derivatives, are abundantly available in this case, provided that m=1 and n=0 and, furthermore, Z represents a hydrogen atom.

In this case, the above Formula (I) can be represented by the following Formula (XIII):

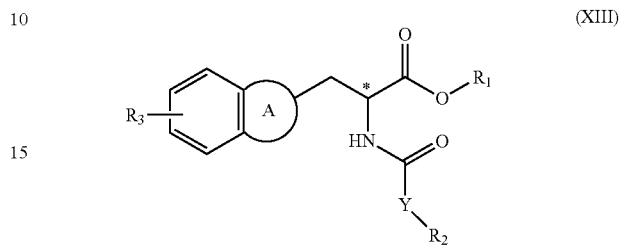

(wherein A, Y, $R_1$, $R_2$, and $R_3$ are the same as defined above, and the position of the asymmetric carbon atom is also denoted by an asterisk).

Synthesis of many different types of compounds represented by the above Formula (XIII) is disclosed in Patent Document 2 (WO 2006/040646), and those compounds are confirmed to have an inhibitory activity against Pin1. The chemical structures of some of the compounds are specifically illustrated as follows.

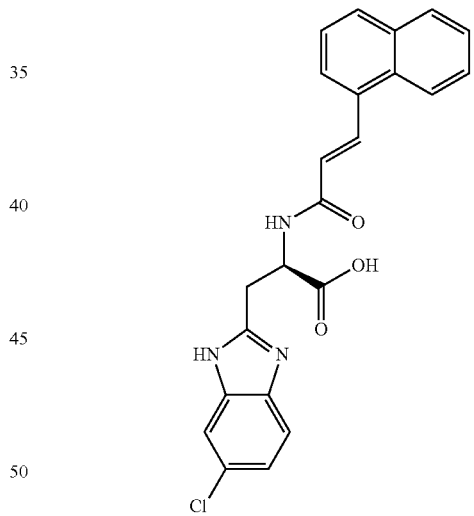

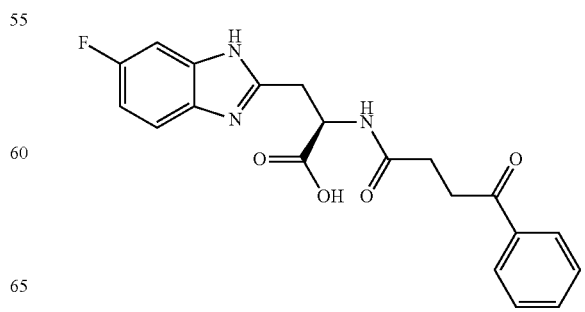

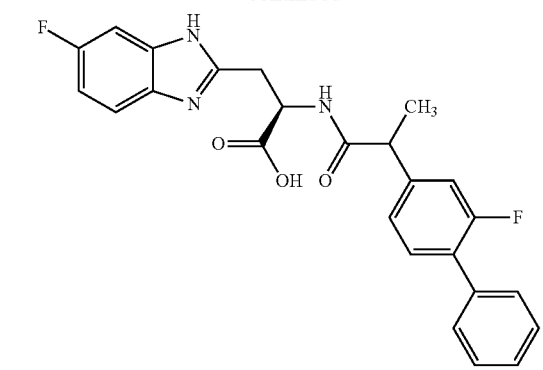
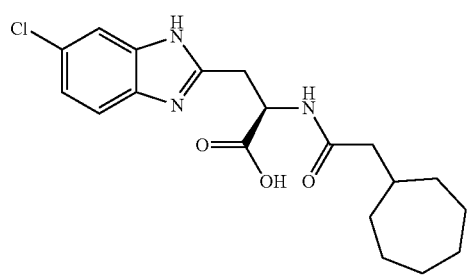
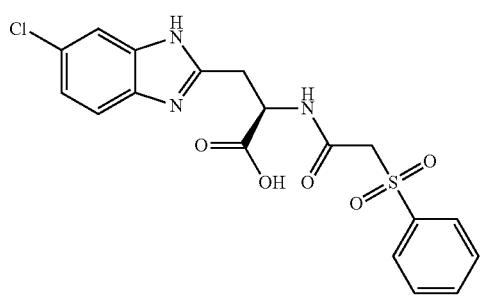
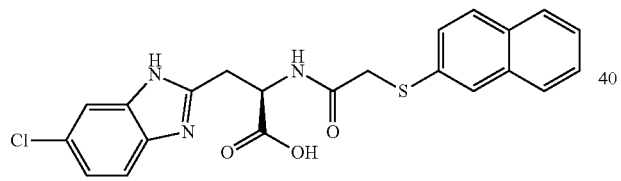
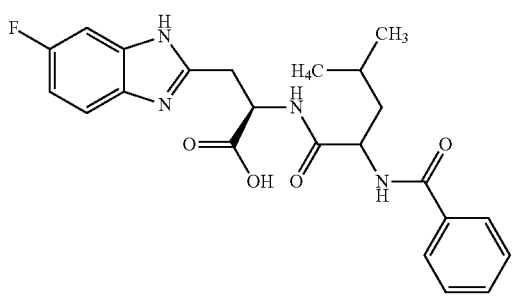
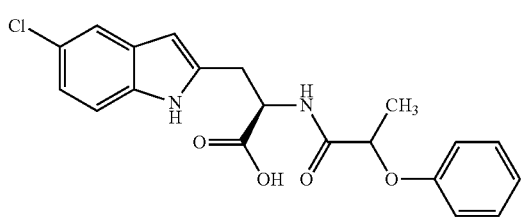

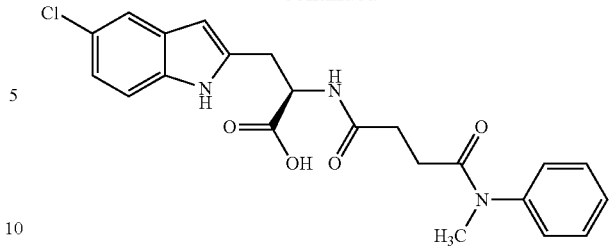

These compounds are compounds represented by the Formula (XIII): Y represents a —CH=CH— group (an alkenylene group), a —CH$_2$—CH$_2$—CO— group (a —CO—R$_6$— group), and a —CH(CH$_3$)— group (a substituted alkylene group), from left to right, for the compounds shown in the upper panel;

additionally, Y represents a —CH$_2$— group (an alkylene group), a —CH$_2$—SO$_2$— group (a —SO$_2$—R$_6$— group), and a —CH$_2$—S— group (a —S—R$_6$— group), from left to right, for the compounds shown in the middle panel; and moreover, Y represents a —CH(CH$_2$CH(CH$_3$)$_2$)—NH—CO— group (a —R$_6$—NR$_5$—CO— group), a —CH(CH$_3$)—O— group (a —O—R$_6$— group), and a —CH$_2$—CH$_2$—CO—N(CH$_3$)— group (a —NR$_5$—CO—R$_6$— group), for the compounds shown in the lower panel.

Synthesis of many different types of compounds represented by the above Formula (XIII) is disclosed in Non-Patent Document 3 (Bioorg. Med. Chem. Lett., 2010, Vol. 20, No. 2, pp. 586-590), and those compounds are confirmed to have an inhibitory activity against Pin1. The chemical structures of some of the compounds are specifically illustrated as follows.

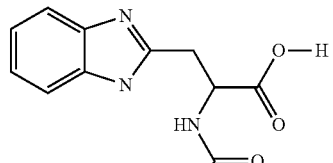
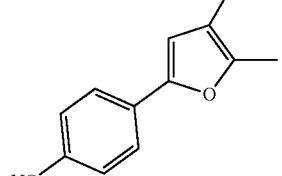
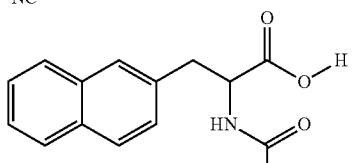
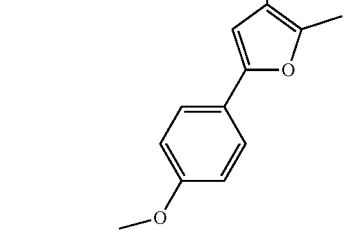

-continued

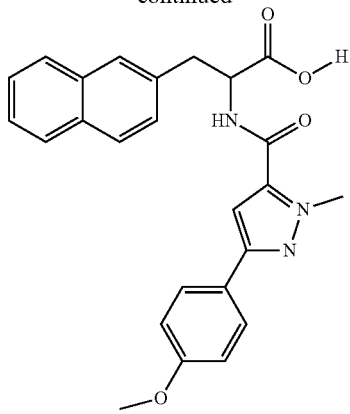

These compounds are all compounds represented by the Formula (XIII), where Y represents a single bond. Among these three compounds, the compound indicated in the middle is a compound named (R)-2-(5-(4-methoxyphenyl)-2-methylfuran-3-carboxamido)-3-(naphthalene-6-yl)propanoic acid, and is hereinafter referred to as "C1."

As a compound represented by the above Formula (XIII), compounds that have been newly synthesized by the inventors as described in Example 1 below can be used. These compounds, in which $R_1$ represents a hydrogen atom to form a carboxyl group, have an inhibitory activity against the function of Pin1. However, even such a compound containing a methyl or benzyl group as $R_1$ can easily be converted into a carboxylic acid by hydrolysis, which is a compound with inhibitory activity against the function of Pin1.

In the compounds synthesized in Example 1 below, Y in the Formula (XIII) represents a single bond, —$CH_2$— group (an alkylene group), or —NH— group.

A compound represented by the above Formula (XIII) can be synthesized by, for example, but not limited to, using an amino acid derivative as a starting material, according to the scheme shown in the following reaction flow chart:

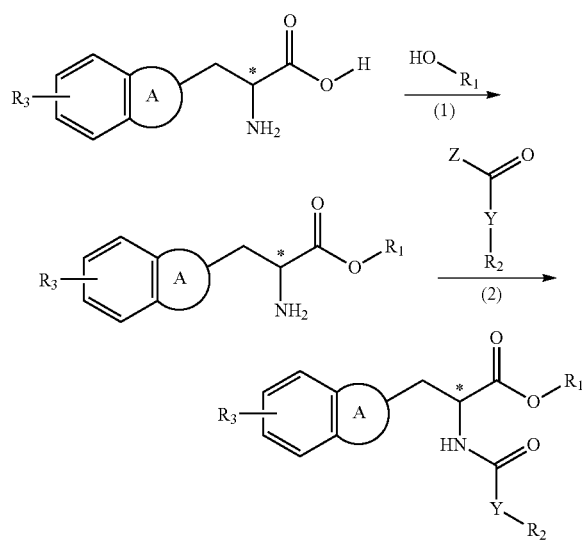

(wherein $R_1$, $R_2$, $R_3$, and Y are the same as defined above, and Z represents a hydroxyl group or a chlorine atom).

In the above scheme, the reaction (1) is a reaction in which the carboxyl group of an amino acid derivative is allowed to react with an $R_1$-containing alcohol through condensation reaction and thereby to attach $R_1$ to the amino acid derivative via an ester bond. Moreover, the reaction (2) is a reaction in which the amino group of the compound prepared by the reaction (1) is allowed to react with a carboxylic acid or acid chloride containing $R_2$ and Y through condensation reaction and thereby to attach Y and $R_2$ to the above compound via an amide bond.

In cases where a compound according to the present invention in which $R_1$ is H is synthesized according to the above scheme, the compound in which $R_1$ is H can be obtained by, for example, hydrolysis of the product after the reactions (1) and (2) to remove $R_1$. Alternatively, the compound in which $R_1$ is H can also be obtained by allowing an amino acid derivative in which $R_1$ is a hydrogen atom to react directly with a carboxylic acid containing $R_2$ and Y through condensation reaction, bypassing the reaction (1).

In compounds represented by the above Formula (I), X may represent a —O—CO— group. Preferably, starting materials for synthesis of the compounds, such as amino acid derivatives, are abundantly available in this case, provided that m=1 and n=0 and, furthermore, Z represents a hydrogen atom.

In this case, the above Formula (I) can be represented by the following Formula (XIV):

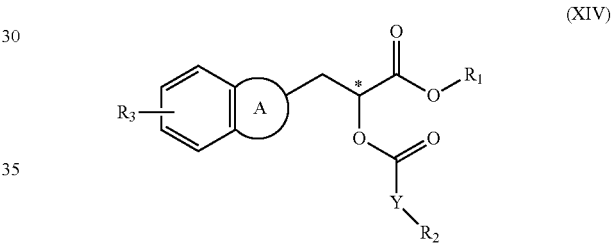

(XIV)

(wherein A, Y, $R_1$, $R_2$, and $R_3$ are the same as defined above, and the position of the asymmetric carbon atom is also denoted by an asterisk).

Compounds represented by the above Formula (XIV) are easily degraded due to the presence of an ester bond, and can be used as therapeutic or prophylactic agents with less side effects. For example, the chemical structure of the compounds can be designed such that the compounds are used as therapeutic or prophylactic agents for fatty liver disease which are absorbed from the digestive tract, transported to the liver through the portal vein, and easily degraded in the liver to provide effects mainly on the liver.

As a compound represented by the above Formula (XIV), compounds that have been newly synthesized by the inventors as described in Example 2 below can be used. These compounds, in which $R_1$ represents a hydrogen atom to form a carboxyl group, have an inhibitory activity against the function of Pin1. However, even such a compound containing a benzyl group as $R_1$ can easily be converted into a carboxylic acid by hydrolysis, which is a compound with inhibitory activity against the function of Pin1.

In the compounds synthesized in Example 1 below, Y in the Formula (XIV) represents a single bond, —$CH_2$— group (an alkylene group), —$CH_2$—O— group (a —O—$R_6$— group), or —CH(NHBoc)—$CH_2$— group (a substituted alkylene group).

A compound represented by the above Formula (XIV) can be synthesized by, for example, but not limited to, using an amino acid derivative as a starting material, according to the scheme shown in the following reaction flow chart:

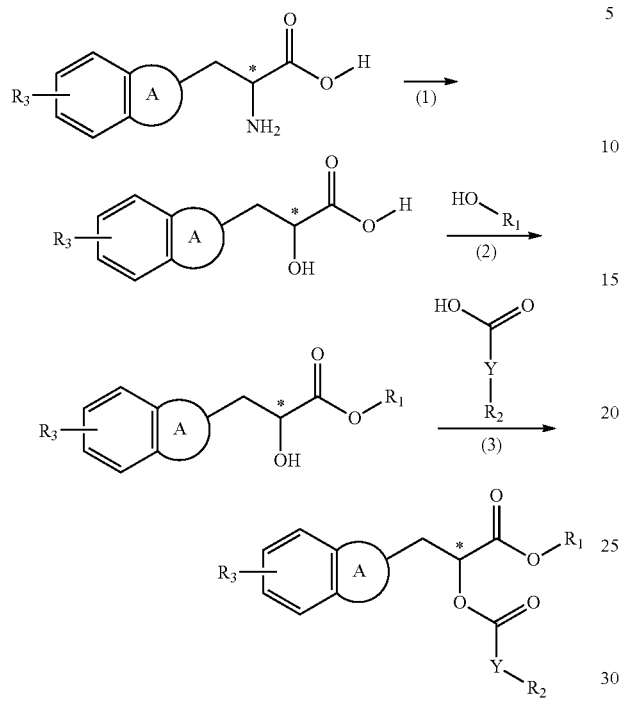

(wherein A, Y, R$_1$, R$_2$, and R$_3$ are the same as defined above).

In the above scheme, the reaction (1) is a reaction in which the amino group of an amino acid derivative used as a starting material is converted into a hydroxy group by a substitution reaction. In addition, the reaction (2) is a reaction in which the carboxylic acid moiety of the hydroxycarboxylic acid derivative is allowed to react with an R$_1$-containing alcohol through condensation reaction and thereby to attach R$_1$ to the hydroxycarboxylic acid derivative via an ester bond. Moreover, the reaction (3) is a reaction in which the hydroxy group generated in the reaction (1) is allowed to react with a carboxylic acid containing R$_2$ and Y through condensation reaction to attach Y and R$_2$ to the above compound via an ester bond.

In cases where a compound according to the present invention in which R$_1$ is H is synthesized according to the above scheme, the compound in which R$_1$ is H can be obtained by, for example, hydrolysis of the product after the reactions (1) to (3) to remove R$_1$. Alternatively, the compound in which R$_1$ is H can also be obtained by allowing a hydroxycarboxylic acid derivative directly with a carboxylic acid containing R$_2$ and Y through condensation reaction, bypassing the reaction (2).

In compounds represented by the above Formula (I), X may represent an —NH— group. Synthesis of many different types of compounds represented by the above Formula (I) where X represents an —NH— group is disclosed in Patent Document 2 (WO 2006/040646), and those compounds are confirmed to have an inhibitory activity against Pin1. The chemical structures of some of the compounds are specifically illustrated as follows.

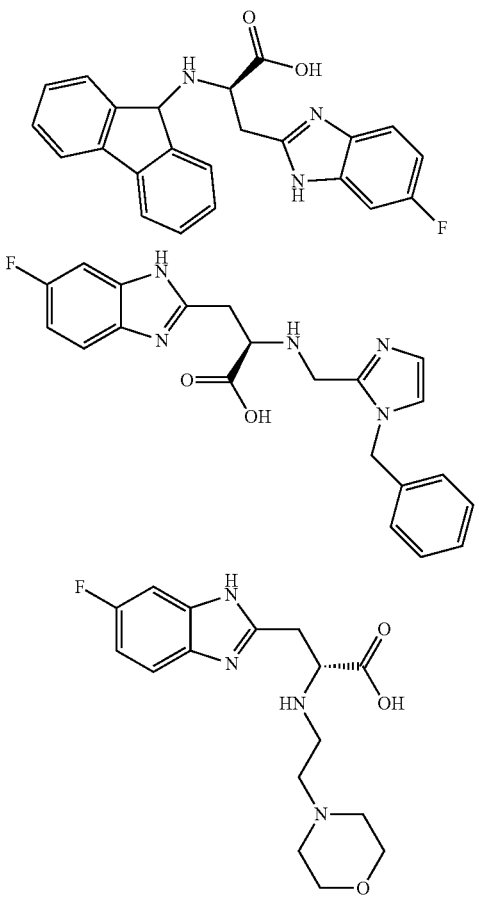

These compounds are compounds represented by the Formula (I), where Y represents a single bond, a —CH$_2$— group (an alkylene group), and a —CH$_2$—CH$_2$— group (an alkylene group), from left to right.

In compounds represented by the above Formula (I), X may represent an —NH—R$_4$— group (R$_4$ represents a C$_{1-5}$ alkylene group or a C$_{2-5}$ alkenylene group).

Synthesis of many different types of compounds represented by the above Formula (I) where X represents an —NH—R$_4$— group is disclosed in Patent Document 2 (WO 2006/040646), and those compounds are confirmed to have an inhibitory activity against Pin1. The chemical structures of some of the compounds are specifically illustrated as follows.

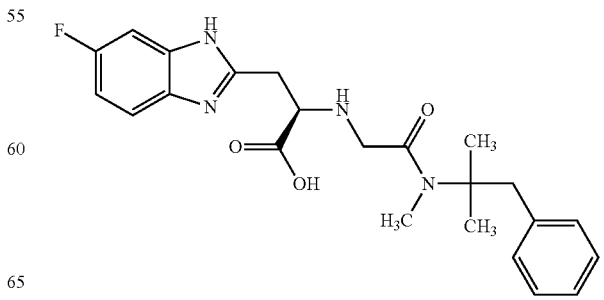

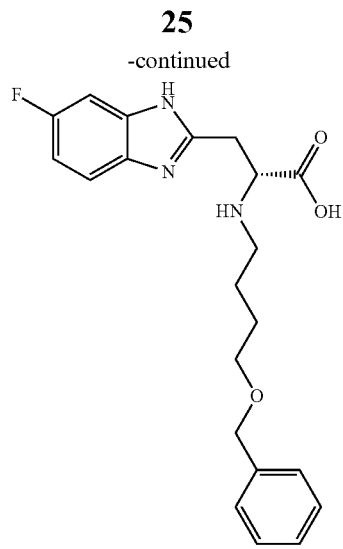

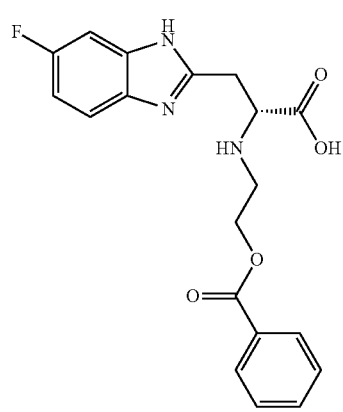

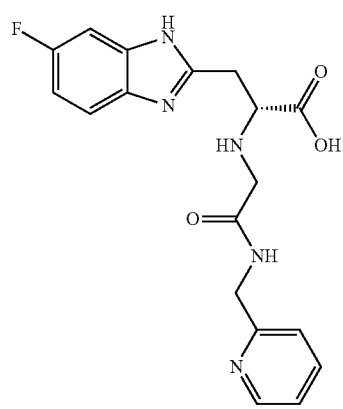

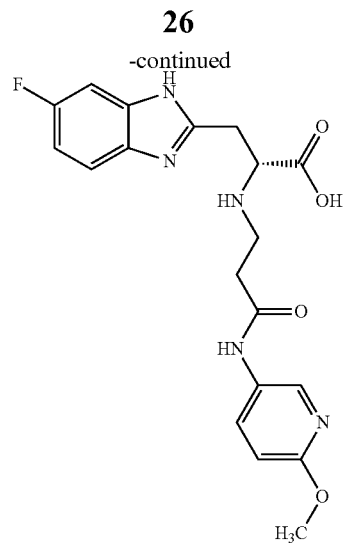

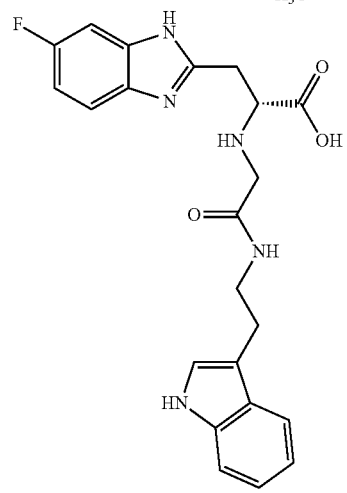

These compounds are compounds represented by the Formula (I): the compound indicated at the left in the upper panel is a compound in which X represents an —NH—CH$_2$— group (an —NH—R$_4$— group) and Y represents a —CO—N(CH$_3$)—C (CH$_3$)$_2$—CH$_2$— group (a —R$_6$—NR—CO— group), and the compound indicated at the center in the upper panel is a compound in which X represents an —NH—(CH$_2$)$_4$— group (an —NH—R$_4$— group) and Y represents a —O—CH$_2$— group (a —O—R$_6$— group), and the compound indicated at the right in the upper panel is a compound in which X represents an —NH—(CH$_2$)$_2$— group and Y represents a —O—CO— group; and the compound indicated at the left in the lower panel is a compound in which X represents an —NH—CH$_2$— group (an —NH—R$_4$— group) and Y represents a —CO—NH—CH$_2$— group (a —R$_6$—NR—CO— group), and the compound indicated at the center in the lower panel is a compound in which X represents an —NH—(CH$_2$)$_2$— group (an —NH—R$_4$— group) and Y represents a —CO—NH— group (a —CO—NR$_5$— group), and the compound indicated at the right in the lower panel is a compound in which X represents an —NH—CH$_2$— group (an —NH—R$_4$— group) and Y represents a —CO—NH—(CH$_2$)$_2$— group (a —R$_6$—NR$_5$—CO— group).

In compounds represented by the above Formula (I), both X and Y may represent a single bond.

Synthesis of many different types of compounds represented by the above Formula (I) where both X and Y represent a single bond is disclosed in Patent Document 2 (WO 2006/040646), and those compounds are confirmed to have an inhibitory activity against Pin1. The chemical structures of some of the compounds are specifically illustrated as follows.

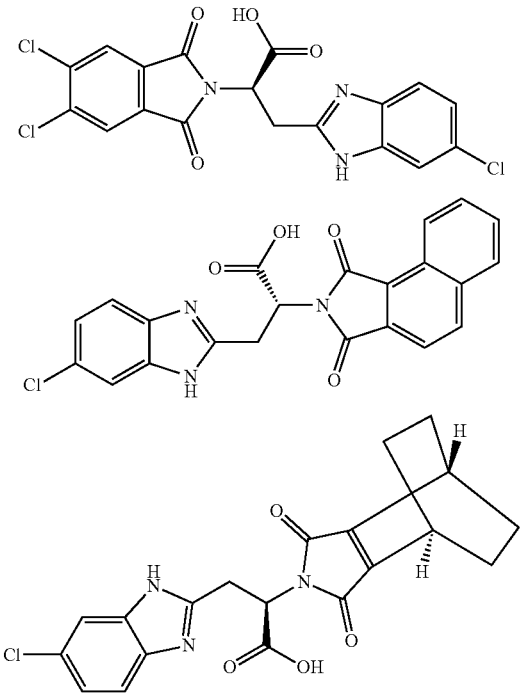

The $R_2$ in the Formula (I) can be a group represented by the Formula (II), and the structure of the Formula (II) is illustrated below.

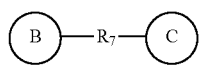

In the Formula (II), the rings B and C independently represent an optionally substituted aryl group, an optionally substituted heterocyclic group, or an optionally substituted cycloalkyl group, and $R_7$ represents a single bond, —O— group, —CO— group, —NH— group, —$SO_2$— group, —CO—NH— group, an optionally substituted $C_{1-3}$ alkylene group, an optionally substituted $C_{2-3}$ alkenylene group, —S—$R_8$— group ($R_8$ represents an optionally substituted $C_{1-2}$ alkylene group), —CO—$R_8$— group, —O—$R_8$— group, or —$SO_2$—$R_8$— group.

Synthesis of many different types of compounds represented by the above Formula (I) where $R_2$ represents a group represented by the Formula (II) is disclosed in Patent Document 2 (WO 2006/040646), and those compounds are confirmed to have an inhibitory activity against Pin1. The chemical structures of some of the compounds are specifically illustrated as follows.

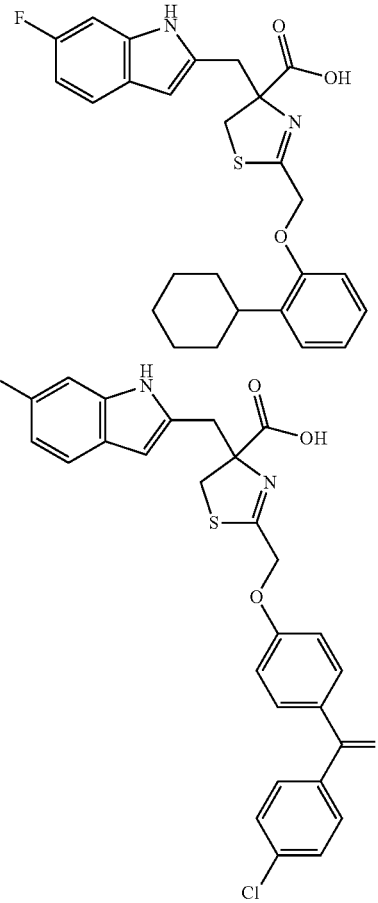

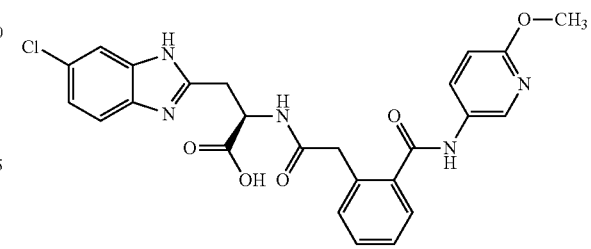

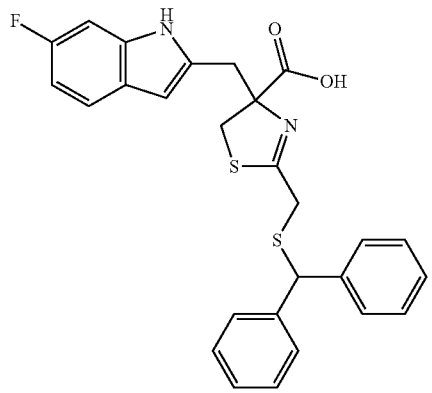

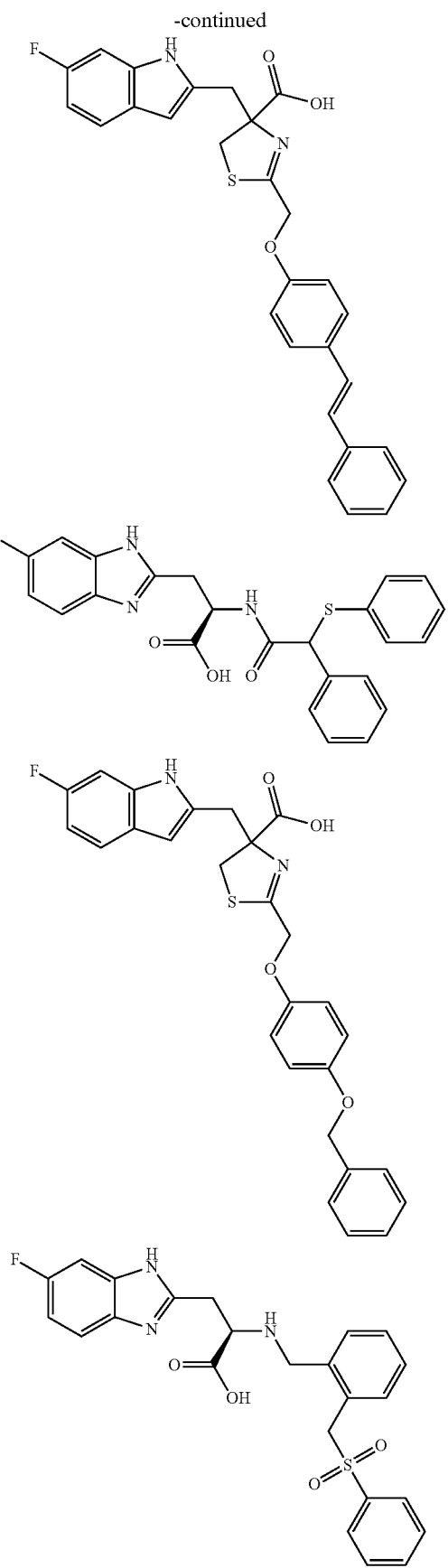

In these compounds, $R_7$, which connects two rings together in the Formula (II), represents a single bond, a —CO— group, and a —CO—NH— group, from left to right, for the compounds shown in the upper panel; additionally, $R_7$ represents a —CH$_2$— group (an alkylene group), a —C=C— group (an alkenylene group), and a —CH$_2$—S— group (a —S—$R_8$— group), from left to right, for the compounds shown in the middle panel; and moreover, $R_7$ represents a —O—CH$_2$— group (a —O—$R_8$— group) and a —CH$_2$—SO$_2$— group (a —SO$_2$—$R_8$— group), from left to right, for the compounds shown in the lower panel.

As a compound represented by the above Formula (I) in which $R_2$ represents a group represented by the Formula (II), compounds that have been newly synthesized by the inventors as described in Example 1 below can also be used.

In the compounds synthesized in Example 1 below, $R_7$ represents a —O— group, —CO— group, or —NH— group.

As a compound represented by the above Formula (I) in which $R_2$ represents a group represented by the Formula (II), compounds that have been newly synthesized by the inventors as described in Example 2 below can also be used.

In the compounds synthesized in Example 2 below, $R_7$ represents a single bond, —O— group, —CH$_2$— group (an alkylene group), or —CH(OH)— group (a substituted alkylene group).

1-2. Inhibitory Activity Against the Function of Pin1

The compounds used as active ingredients in the present invention have a chemical structure represented by the Formula (I) and an inhibitory activity against the function of Pin1.

In this respect, the inhibitory activity against the function of Pin1 means inhibiting the isomerase activity of Pin1 and/or the activity of Pin1 to associate or interact with another protein, such as IRS-1.

The result of, for example, X-ray crystallographic analysis on a compound having a basic structure represented by the Formula (I) and the associated Pin has also indicated that the compound having the chemical structure represented by the Formula (I) is not a compound that inhibits various enzymes, as Juglone does, but is a compound specific for Pin1 (for example, Non-Patent Document 3).

To determine whether a compound used as an active ingredient has an inhibitory activity against the function of Pin1 or not, the activity of the putative Pin1 inhibitor according to the present invention to inhibit the function of Pin1 can be measured by, for example, but not limited to, examining AMPK (AMP-activated protein kinase) phosphorylation level as an index (see Yusuke Nakatsu et al., Journal of Biological Chemistry, 2015, Vol. 290, No. 40, pp. 24255-24266). Alternatively, the activity of the putative Pin1 inhibitor according to the present invention to inhibit the function of Pin1 can also be measured by detecting a change in the isomerase activity of Pin1 against a peptide substrate as a change in absorbance (see Hailong Zhao et al. Bioorganic & Medicinal Chemistry, 2016, Vol. 24, pp. 5911-5920). Alternatively, the activity of the putative Pin1 inhibitor according to the present invention to inhibit the function of Pin1 can also be measured by detecting the association of the inhibitor with Pin1, which competes with the association of Pin1 with a peptide substrate (see Shuo Wei et al., Nature Medicine, Vol. 21, No. 5, pp. 457-466, online methods).

1-3. Pharmaceutically Acceptable Salts

Therapeutic or prophylactic agents for fatty liver disease according to the present invention contain a compound represented by the Formula (I) or a pharmaceutically acceptable salt thereof as an active ingredient.

In this respect, examples of the pharmaceutically acceptable salt" can include, but are not limited to, sodium, potassium, and ammonium salts, in cases where the compound has an acidic functional group in the molecule. Additionally, in cases where the compound has a basic functional group in the molecule, the pharmaceutically acceptable salt of the compound can include hydrochloride, phosphate, acetate, phthalate, fumarate, and oxalate salts.

1-4. Indications

Fatty liver disease, which is an indication for therapeutic or prophylactic agents according to the present invention, is also called "fatty liver" and is a condition with excessive hepatic accumulation of neutral fats. Fatty liver disease includes alcoholic fatty liver and non-alcoholic fatty liver disease (NAFLD). Non-alcoholic fatty liver disease (NAFLD) is a condition characterized by fat accumulation, similar to that found in cases of alcoholic fatty liver, and observed even in patients who have no history of alcohol intake sufficient to induce liver injury, and classified as metabolic syndrome. Non-alcoholic fatty liver disease (NAFLD) includes a mild form of non-alcoholic fatty liver disease, simple steatosis, and a severe form of non-alcoholic fatty liver disease involving liver tissue inflammation and fibrosis, non-alcoholic steatohepatitis (NASH).

The compounds used as active ingredients in the present invention can inhibit the function of Pin1 as a mechanism of action to reduce fat accumulation, and therefore can be used as therapeutic or prophylactic agents for fatty liver disease.

The therapeutic or prophylactic agents for fatty liver disease according to the present invention can be administered as therapeutic or prophylactic agents not only to patients diagnosed with fatty liver disease but also to patients suspected of having or at risk of fatty liver disease.

Additionally, the therapeutic or prophylactic agents for fatty liver disease according to the present invention can be suitably used for inhibition of liver inflammation and fibrosis, particularly for treatment or prevention of non-alcoholic steatohepatitis (NASH).

1-5. Dosage Forms

A therapeutic or prophylactic agent for fatty liver disease according to the present invention can be prepared as a pharmaceutical composition by combining the compound or a pharmaceutically acceptable salt thereof as an active ingredient with a pharmaceutically acceptable carrier, and may be made in the form of, for example, but not limited to, tablets, granules, capsules, powders, liquids, injection solutions, suppositories, patches, eye drops, and inhalants.

Suitable dosage forms for oral administration can be, for example, tablets, granules, capsules, powders, and liquids. Moreover, the therapeutic or prophylactic agent can also be administered in the form of injection solution directly to the liver by, for example, tube feeding, from the viewpoint of allowing the therapeutic or prophylactic agent to act directly on the liver and thereby to reduce side effects.

As a pharmaceutically acceptable carrier that can be used in therapeutic or prophylactic agents for fatty liver disease according to the present invention, various inorganic or organic carrier materials can be used. When the pharmaceutical composition is prepared in solid formulation, such as a tablet or a granule, an excipient, a lubricant, a binder, a disintegrator, and the like can be used. When the pharmaceutical composition is prepared in liquid formulation, such as a liquid or an injection solution, a solvent, a solubilizing agent, a suspending agent, a buffering agent, and the like can be used.

Moreover, additives such as antioxidant, antiseptic agent, and coloring agent can also be used as necessary.

Non-limiting examples of an excipient that can be used include lactose, D-mannitol, and starch; non-limiting examples of a lubricant that can be used include magnesium stearate and talc; non-limiting examples of a binder that can be used include crystalline cellulose and gelatin; non-limiting examples of a disintegrator that can be used include carboxymethyl cellulose.

Moreover, examples of a solvent that can be used include distilled water, alcohols, and propylene glycol; examples of a solubilizing agent that can be used include polyethylene glycol and ethanol; examples of a suspending agent that can be used include stearyl triethanolamine and sodium lauryl sulfate; examples of a buffering agent that can be used include phosphate and acetate salts.

The therapeutic or prophylactic agents for fatty liver disease according to the present invention should preferably be administered to a patient at a daily dose of 0.01 to 100 mg, more preferably 0.1 to 10 mg, of active ingredient per kg of body weight.

The therapeutic or prophylactic agents for fatty liver disease according to the present invention may contain a compound according to the present invention or a pharmaceutically acceptable salt thereof and further contain active ingredients in at least one or more drugs selected from the group of therapeutic or prophylactic agents for fatty liver disease.

Examples of the active ingredients that can be used include, but are not limited to, vitamin E, and drugs under clinical trial at the timing of this application, such as obeticholic acid (6-ethyl-chenodeoxycholic acid), elafibranor, selonsertib, saroglitazar, lanifibranor, semaglutide, and pemafibrate.

Additionally, the therapeutic or prophylactic agents for fatty liver disease according to the present invention can be used in combination with other therapeutic or prophylactic agents for fatty liver disease.

2. Therapeutic or Prophylactic Agents for Obesity

Therapeutic or prophylactic agents for obesity according to the present invention contain a compound represented by the Formula (I) or a pharmaceutically acceptable salt thereof as an active ingredient.

The structure of the compound represented by the Formula (I) is as described in the above section 1-1, while the pharmaceutically acceptable salt thereof is as described in the above section 1-3.

The therapeutic or prophylactic agents for obesity according to the present invention have an effect to reduce accumulation of body fat and thereby to treat or prevent obesity. Such beneficial effects are based on inhibition of Pin1 function as the mechanism of action of the compound represented by the Formula (I) or the pharmaceutically acceptable salt thereof.

In the present invention, "obesity" refers to a condition with excessive fat accumulation in the internal organs or under the skin, which can be diagnosed with, for example, abdominal fat area measured by abdominal CT scanning. The therapeutic or prophylactic agents for obesity according to the present invention can be administered as therapeutic or prophylactic agents for obesity not only to patient diagnosed with obesity but also to patients suspected of having or at risk of obesity.

The therapeutic or prophylactic agents for obesity according to the present invention may be formulated in various dosage forms, which are combined with pharmaceutically acceptable carriers, as described in the above section 1-5.

The therapeutic or prophylactic agents for obesity according to the present invention should preferably be administered to a patient at a daily dose of 0.01 to 100 mg, more preferably 0.1 to 10 mg, of active ingredient per kg of body weight.

The therapeutic or prophylactic agents for obesity according to the present invention may contain a compound according to the present invention or a pharmaceutically acceptable salt thereof and further contain active ingredients in at least one or more drugs selected from the group of therapeutic or prophylactic agents for obesity.

Examples of the active ingredients that can be used include, but are not limited to, cetilistat, orlistat, and lorcaserin.

Additionally, the therapeutic or prophylactic agents for obesity according to the present invention can be used in combination with other therapeutic or prophylactic agents for obesity.

Now, the present invention will be described in detail by reference to examples, but the present invention is not limited thereto.

EXAMPLES

Example 1

(Synthesis of Amide Compounds)

(Example 1-1) Synthesis of Intermediates

Intermediates (H-34, H-47, and H-48) used for the synthesis of compounds used as active ingredients in the present invention were produced.
Thionyl chloride (4.9 g, 3.0 mL, 41 mmol) was added to a solution of D-naphthylalanine (5.0 g, 23.2 mmol) in methanol (100 mL) at room temperature, and the resulting mixture was stirred at the same temperature for 16 hours. The mixture was concentrated under reduced pressure. Toluene was added to the residue, and thionyl chloride was removed from the residue by repeating the concentration step under reduced pressure several times to give H-34 represented by the following structural formula as a white powder (6.2 g, 23.2 mmol, 100%).

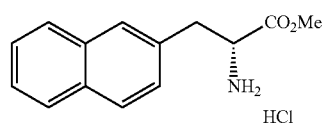

H-34

To a solution of H-34 hydrochloride (400 mg, 1.4 mmol) in dichloromethane (3 mL), saturated aqueous sodium bicarbonate solution (3 mL) at 0° C. and then a solution of triphosgene (178 mg, 0.6 mmol) in dichloromethane (1 mL) at the same temperature were added, and the resulting mixture was stirred at the same temperature for 15 minutes. The mixture was extracted with chloroform. The organic layer was washed with saturated brine, dried over anhydrous magnesium sulfate, and then filtered and concentrated under reduced pressure to give H-48 represented by the following structural formula. The obtained product was used without further purification at the next step.

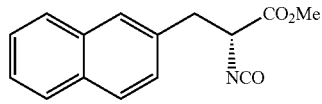

H-48

A solution of D-naphthylalanine (3.0 g, 13.9 mmol), benzyl alcohol (22.5 g, 21 mL, 209 mmol), and p-toluenesulfonic acid monohydrate (4.0 g, 20.9 mmol) in benzene (180 mL) was azeotropically dehydrated under reflux with stirring for 3 days. The mixture was cooled down to room temperature, diluted with ethyl acetate, and then washed three times with saturated sodium bicarbonate solution. The organic layer was washed with saturated brine, dried over anhydrous magnesium sulfate, and then filtered and concentrated under reduced pressure. Hydrochloric acid at a concentration of 1 M was added to the residue, and the obtained powder was suspended in ether, and then filtered under reduced pressure. The solid was washed several times with ether to give H-47 represented by the following structural formula as a white powder (4.59 g, 13.5 mmol, 97%).

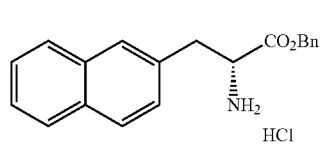

H-47

(Example 1-2) Synthesis of H-144

To a solution of H-34 hydrochloride (200 mg, 0.753 mmol) in dichloromethane (4 mL), triethylamine (183 mg, 0.25 mL, 1.81 mmol) at room temperature and then 9H-carbazole-9-carbonyl chloride (207 mg, 0.904 mmol) at the same temperature were added, and the resulting mixture was stirred at the same temperature for 2 days. Water was added to the mixture, and the resulting mixture was extracted with ethyl acetate. The organic layer was washed with saturated brine, dried over anhydrous magnesium sulfate, and then filtered and concentrated under reduced pressure. The residue was purified by silica gel column chromatography (hexane:ethyl acetate, 4:1) to give H-144 as a white crystal (210 mg, 0.381 mmol, 66%).

The measured NMR spectrum and HR-ESI-MS result of H-144 are described below. $^1$H NMR (400 MHz, CDCl$_3$) δ 3.45 (1H, dd, J=14.2, 6.5 Hz), 3.61 (1H, dd, J=14.2, 5.4 Hz), 3.86 (3H, s), 5.19 (1H, ddd, J=7.4, 6.5, 5.4 Hz), 6.24 (1H, d, J=7.4 Hz), 7.20-7.31 (4H, m), 7.34 (1H, dd, J=8.7, 1.8 Hz), 7.45-7.51 (2H, m), 7.69 (1H, s), 7.71-7.79 (3H, m), 7.80-7.86 (2H, m), 7.95-7.99 (2H, m); HRESIMS calcd for C$_{27}$H$_{22}$N$_2$O$_3$Na [M+Na]$^+$445.1528, found 445.1530.

The identified chemical structure of H-144 is indicated below.

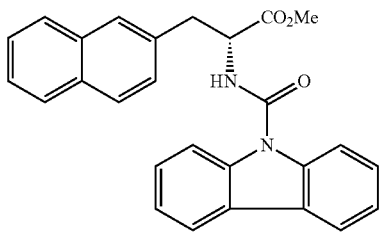

H-144

(Example 1-3) Synthesis of H-163

To a solution of H-144 (177 mg, 0.42 mmol) in THF (5 mL), an aqueous lithium hydroxide solution (1 M, 1.7 mL, 1.7 mmol) was added at room temperature, and the resulting mixture was stirred at the same temperature for 2 hours. The mixture was neutralized by adding 1 M hydrochloric acid thereto, and then extracted with ethyl acetate. The organic layer was washed with saturated brine, dried over anhydrous magnesium sulfate, and then filtered and concentrated under reduced pressure to give H-163 as a yellow crystal (158 mg, 0.386 mmol, 92%).

The measured NMR spectrum and HR-ESI-MS result of H-163 are described below. $^1$H NMR (400 MHz, DMSOd$_6$) δ 3.28 (1H, dd, J=13.7, 11.4 Hz), 3.51 (1H, dd, J=13.7, 4.5 Hz), 4.80 (1H, ddd, J=11.4, 8.2, 4.5 Hz), 7.17 (2H, t, J=7.4 Hz), 7.24 (2H, t, J=7.4 Hz), 7.46-7.55 (4H, m), 7.61 (1H, d, J=8.7 Hz), 7.86-7.96 (4H, m), 8.09 (2H, d, J=7.7 Hz), 8.72 (1H, d, J=8.2 Hz); HRESIMS calcd for $C_{26}H_{20}N_2O_3Na$ [M+Na]$^+$431.1372, found 431.1369.

The identified chemical structure of H-163 is indicated below.

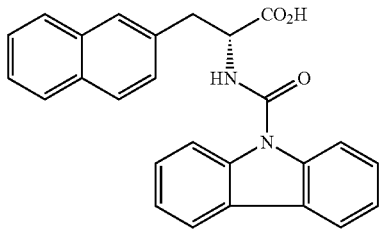

H-163

(Example 1-4) Evaluation of Pin Inhibition Activity

To evaluate the inhibitory activity of each synthesized compound against the function of Pin1, a cell-based assay was performed according to the method previously developed by the inventors (Yusuke Nakatsu et al., Journal of Biological Chemistry, 2015, Vol. 290, No. 40, pp. 24255-24266), in which the phosphorylation level of AMPK (AMP-activated protein kinase), a protein whose phosphorylation is inhibited by Pin1, was examined as an index.

Briefly, 293T cells were plated on a collagen-coated 24-well plate. Forty-eight hours later, each compound synthesized in the preceding example (at 100 μM) was added to the plate, and the plate was left to stand in an incubator for 30 minutes. Subsequently, 10 mM 2-DG was added to the plate, and one hour later, each sample was collected with a buffer containing mercaptoethanol and SDS.

SDS-PAGE and blotting were performed, and blocking was then performed with 3% BSA for 1 hour, according to conventional protocols. Subsequently, a pAMPK antibody (Cell Signaling; diluted 1:2000 in Can Get Signal Solution 1, Toyobo) as a primary antibody, and an HRP-linked anti rabbit IgG (GE Healthcare; diluted 1:4000 in Can Get Signal Solution 2, Toyobo) as a secondary antibody were allowed to react at ambient temperature for 1 hour prior to detection.

The inhibitory activity against the function of Pin1 was evaluated by comparing the inhibition levels between each compound and a known Pin1 inhibitor, C1, as indicated below:

(+++): a higher level of AMPK phosphorylation is promoted, as compared with C1;

(++): a similar level of AMPK phosphorylation is promoted, as compared with C1;

(+): a lower level of AMPK phosphorylation is promoted, as compared with C1;

(−): no or almost no promotion is found in AMPK phosphorylation.

When H-163 synthesized in Example 1-3 was evaluated by this method, the result was rated as (++), and a similar level of AMPK phosphorylation was promoted, as compared with C1.

The activity was not measured in H-144, which is an ester formed by attachment of a methyl group to the carboxylic acid of H-163. This ester can be easily hydrolyzed into a carboxylic acid, which is an active compound.

(Example 1-5) Synthesis of Other Amide Compounds

Multiple amide compounds were synthesized using the intermediates synthesized in Example 1-1 by synthesis methods similar to those in Examples 1-2 and 1-3. Then, the inhibitory activity of the synthesized compounds against Pin1 was evaluated by the same evaluation method as that in Example 1-4. The chemical structures and activity evaluation results of the synthesized compounds are shown in the following tables.

TABLE 1

| Compound No. | Structural formula | Pin1 inhibition activity |
|---|---|---|
| H-53 | ![structure] | Not measured (Hydrolysis causes conversion to H-62, which is active) |

TABLE 1-continued

| Compound No. | Structural formula | Pin1 inhibition activity |
|---|---|---|
| H-62 | (naphthalene-CH2-CH(CO2H)-NH-C(=O)-naphthalene-CO2Me) | + |
| H-85 | (naphthalene-CH2-CH(CO2Me)-NH-C(=O)-9H-fluorene) | Not measured (Hydrolysis causes conversion to H-109, which is active) |
| H-101 | (naphthalene-CH2-CH(CO2H)-NH-C(=O)-9-hydroxy-9H-fluorene) | ++ |

TABLE 2

| Compound No. | Structural formula | Pin1 inhibition activity |
|---|---|---|
| H-91 | (naphthalene-CH2-CH(CO2Me)-NH-C(=O)-CH2-9H-fluorene) | Not measured (Hydrolysis causes conversion to H-103, which is active) |
| H-103 | (naphthalene-CH2-CH(CO2H)-NH-C(=O)-CH2-9H-fluorene) | +++ |

TABLE 2-continued

| Compound No. | Structural formula | Pin1 inhibition activity |
|---|---|---|
| H-105 | (naphthalene-CH2-CH(CO2Bn)-NH-C(=O)-9H-fluorene) | − (Hydrolysis causes conversion to H-109, which is active) |
| H-109 | (naphthalene-CH2-CH(CO2H)-NH-C(=O)-9H-fluorene) | +++ |

TABLE 3

| Compound No. | Structural formula | Pin1 inhibition activity |
|---|---|---|
| H-129 | (naphthalene-CH2-CH(CO2Me)-NH-C(=O)-N(phenyl)2) | Not measured (Hydrolysis causes conversion to H-161, which is active) |
| H-161 | (naphthalene-CH2-CH(CO2H)-NH-C(=O)-N(phenyl)2) | ++ |
| H-138 | (naphthalene-CH2-CH(CO2Me)-NH-C(=O)-CH2-naphthalene) | Not measured (Hydrolysis causes conversion to H-158, which is active) |
| H-158 | (naphthalene-CH2-CH(CO2H)-NH-C(=O)-CH2-naphthalene) | ++ |

TABLE 4

| Compound No. | Structural formula | Pin1 inhibition activity |
| --- | --- | --- |
| H-143 | (naphthyl-CH2-CH(CO2Me)-NH-C(=O)-N(phenoxazine)) | Not measured (Hydrolysis causes conversion to H-162, which is active) |
| H-162 | (naphthyl-CH2-CH(CO2H)-NH-C(=O)-N(phenoxazine)) | ++ |
| H-144 | (naphthyl-CH2-CH(CO2Me)-NH-C(=O)-N(carbazole)) | Not measured (Hydrolysis causes conversion to H-163, which is active) |
| H-163 | (naphthyl-CH2-CH(CO2H)-NH-C(=O)-N(carbazole)) | ++ |

TABLE 5

| Compound No. | Structural formula | Pin1 inhibition activity |
| --- | --- | --- |
| H-156 | (naphthyl-CH2-CH(CO2Me)-NH-C(=O)-N(dibenzazepine, unsaturated)) | Not measured (Hydrolysis causes conversion to H-164, which is active) |
| H-164 | (naphthyl-CH2-CH(CO2H)-NH-C(=O)-N(dibenzazepine, unsaturated)) | + |
| H-178 | (naphthyl-CH2-CH(CO2H)-NH-C(=O)-N(dibenzazepine, saturated)) | +++ |

TABLE 5-continued

| Compound No. | Structural formula | Pin1 inhibition activity |
| --- | --- | --- |
| H-287 | (naphthyl-CH2-CH(CO2Me)-NH-C(=O)-NH-phenyl-O-phenyl) | Not measured (Hydrolysis causes conversion to H-334, which is active) |

TABLE 6

| Compound No. | Structural formula | Pin1 inhibition activity |
| --- | --- | --- |
| H-334 | (naphthyl-CH2-CH(CO2H)-NH-C(=O)-NH-phenyl-O-phenyl) | +++ |
| H-291 | (naphthyl-CH2-CH(CO2Me)-NH-C(=O)-NH-phenyl-C(=O)-phenyl) | Not measured (Hydrolysis causes conversion to H-341, which is active) |
| H-341 | (naphthyl-CH2-CH(CO2H)-NH-C(=O)-NH-phenyl-C(=O)-phenyl) | ++ |

TABLE 6-continued

| Compound No. | Structural formula | Pin1 inhibition activity |
|---|---|---|
| H-521 | (2-naphthyl)-CH2-C*H(CO2Me)-NH-C(=O)-CH2-N(carbazole) | + |

TABLE 7

| Compound No. | Structural formula | Pin1 inhibition activity |
|---|---|---|
| H-536 | (2-naphthyl)-CH2-C*H(CO2H)-NH-C(=O)-CH2-N(carbazole) | + |

The activity was not measured in H-53, H-91, H-129, H-138, H-143, H-144, H-156, H-287, and H-291, which are esters formed by attachment of a methyl or benzyl group to the carboxylic acids of H-62, H-103, H-161, H-158, H-162, H-163, H-164, H-334, and H-341, respectively. These esters can be easily hydrolyzed into carboxylic acids, which are active compounds.

Additionally, the activity was not measured in H-85, which is an ester formed by attachment of a methyl group to the carboxylic acid of H-109. This ester can be easily hydrolyzed into a carboxylic acid, which is an active compound.

The result of the cell-based assay indicated that H-105 has no Pin1 inhibition activity, but H-105 is an ester formed by attachment of a benzyl group to the carboxylic acid of H-109. This ester can be easily hydrolyzed into a carboxylic acid, which is an active compound.

Example 2

(Synthesis of Ester Compounds)

(Example 2-1) Synthesis of Intermediates

An intermediate (H-26) used for the synthesis of compounds used as active ingredients in the present invention was produced.

To a suspension of D-naphthylalanine (10.3 g, 47.9 mmol) in water (40 mL), 1M sulfuric acid (60 mL) and acetone (160 mL) were added at room temperature, and the resulting mixture was cooled down to −5° C., and a solution of sodium nitrite (9.9 g, 144 mmol) in water (40 mL) was slowly added to the mixture. The resulting mixture was stirred at −5° C. for 30 minutes, and then at room temperature for further 16 hours. After acetone was removed under reduced pressure, the mixture was extracted with ethyl acetate. The organic layer was washed with saturated brine, dried over anhydrous magnesium sulfate, and then filtered and concentrated under reduced pressure to give a compound (H-18) represented by the following structural formula. This compound was used without further purification at the next step.

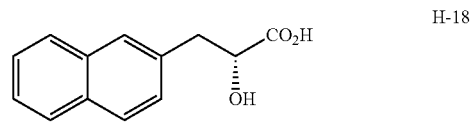 [SMILES: O=C(O)[C@H](O)Cc1ccc2ccccc2c1]

H-18

A solution of the crude H-18 product, benzyl alcohol (5.18 g, 4.9 mL, 47.9 mmol), and p-toluenesulfonic acid monohydrate (912 mg, 4.8 mmol) in benzene (150 mL) was azeotropically dehydrated under reflux with stirring for 8 hours. The mixture was cooled down to room temperature, saturated sodium bicarbonate solution was then added to the mixture, and the resulting mixture was extracted with ethyl acetate. The organic layer was washed with saturated brine, dried over anhydrous magnesium sulfate, and then filtered and concentrated under reduced pressure. The residue was purified by silica gel column chromatography (hexane:ethyl acetate, 4:1) to give a compound (H-26) represented by the following structural formula as a white crystal (11.7 g, 38.3 mmol, 80%). The crystal was dissolved in ether, and the resulting solution was left to stand to separate a crystal, and the resulting crystal was filtered and then washed with a mixed solvent of hexane and ether (4:1).

The measured NMR spectrum and HR-ESI-MS result of H-26 are described below.

$^1$H NMR (400 MHz, CDCl$_3$) δ 3.16 (1H, dd, J=13.7, 6.4 Hz), 3.30 (1H, dd, J=13.7, 4.6 Hz), 4.59 (1H, dd, J=6.4, 4.6 Hz), 5.16 (1H, d, J=12.3 Hz), 5.21 (1H, d, J=12.3 Hz), 7.26-7.39 (6H, m), 7.42-7.49 (2H, m), 7.62 (1H, s), 7.71-7.76 (2H, m), 7.78-7.83 (1H, m); $^{13}$C NMR (100 MHz, CDCl$_3$) δ 40.6, 67.4, 71.3, 125.5, 126.0, 126.9, 127.6, 127.7, 128.0, 128.2, 128.5, 128.6, 132.4, 133.4, 133.7, 134.9, 173.9; HRESIMS calcd for C$_{20}$H$_{18}$O$_3$Na [M+Na]$^+$ 329.1154, found 329.1151.

The identified chemical structure of H-26 is indicated below.

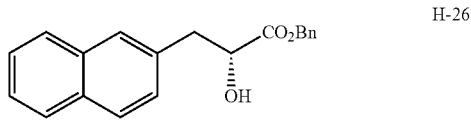 [SMILES: O=C(OCc1ccccc1)[C@H](O)Cc1ccc2ccccc2c1]

H-26

(Example 2-2) Synthesis of H-31

To a solution of H-26 (150 mg, 0.49 mmol), fluorene-9-carboxylic acid (124 mg, 0.588 mmol), and 4-dimethylaminopyridine (6.0 mg, 0.049 mmol) in dichloromethane (5 mL), 1-ethyl-3-(3-dimethylaminopropyl)carbodiimide hydrochloride (122 mg, 0.64 mmol) was added at room temperature, and the resulting mixture was stirred at the same temperature for 8 hours. Water was added to the mixture, and the resulting mixture was extracted with ethyl acetate. The organic layer was washed with saturated brine, dried over anhydrous magnesium sulfate, and then filtered and concentrated under reduced pressure. The residue was purified by silica gel column chromatography (hexane:ethyl acetate, 6:1) to give H-22 as a pale yellow crystal (191 mg, 0.384 mmol, 78%).

The measured NMR spectrum and HR-ESI-MS result of H-22 are described below.

$^1$H NMR (400 MHz, CDCl$_3$) δ 3.26 (1H, dd, J=14.2, 8.7 Hz), 3.45 (1H, dd, J=14.2, 4.1 Hz), 4.85 (1H, s), 5.12 (1H, d, J=12.3 Hz), 5.19 (1H, d, J=12.3 Hz), 5.44 (1H, dd, J=8.7, 4.1 Hz), 7.02 (1H, td, J=7.3, 0.9 Hz), 7.12-7.21 (5H, m), 7.26-7.40 (5H, m), 7.43-7.53 (3H, m), 7.55 (1H, s), 7.66-7.73 (4H, m), 7.80-7.85 (1H, m); $^{13}$C NMR (100 MHz, CDCl$_3$) δ 37.3, 53.0, 67.2, 73.6, 119.86, 119.88, 125.5, 125.6, 125.7, 126.0, 127.2, 127.3, 127.6, 127.7, 128.0, 128.12, 128.16, 128.19, 128.3, 128.4, 128.5, 133.1, 133.3, 135.0, 140.0, 140.1, 141.3, 141.4, 169.1, 170.5; HRESIMS calcd for C$_{34}$H$_{26}$O$_4$Na [M+Na]$^+$521.1729, found 521.1732.

The identified chemical structure of H-22 is indicated below.

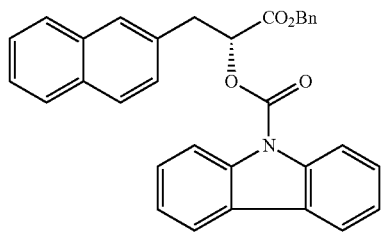

H-22

To a solution of H-22 (188 mg, 0.377 mmol) in THF (6 mL), 5% Pd/C (100 mg) was added, and the resulting mixture was stirred under hydrogen atmosphere at room temperature for 16 hours. The reaction mixture was filtered using celite. After the residue was washed with ethyl acetate, the resulting wash solution was concentrated under reduced pressure to give H-31 as a white gel (140 mg, 0.343 mmol, 91%) (>99% ee, AD-H column, hexane:isopropanol, 5:1).

The specific rotation, IR spectrum, measured NMR spectrum, and HR-ESI-MS result of H-31 are described below.

[α]$_D^{25}$=−63.6 (c 0.38, CHCl$_3$); IR (KBr) 3449, 1760, 1719 cm$^{-1}$; $^1$H NMR (400 MHz, CDCl$_3$) δ 3.26 (1H, dd, J=14.1, 9.6 Hz), 3.42 (1H, dd, J=14.1, 3.6 Hz), 4.86 (1H, s), 5.41 (1H, dd, J=9.6, 3.7 Hz), 6.92 (1H, t, J=6.9 Hz), 7.16 (1H, d, J=7.3 Hz), 7.18-7.24 (2H, m), 7.32 (1H, t, J=7.8 Hz), 7.38 (1H, t, J=7.7 Hz), 7.46-7.52 (3H, m), 7.59 (1H, s), 7.68-7.76 (4H, m), 7.80-7.86 (1H, m); $^{13}$C NMR (100 MHz, CDCl$_3$) δ 37.1, 53.0, 73.2, 119.9, 125.5, 125.6, 125.8, 126.1, 127.1, 127.3, 127.6, 127.7, 128.1, 128.2, 128.3, 132.5, 133.0, 133.3, 139.9, 140.0, 141.3, 141.4, 170.6, 174.8; HRESIMS calcd for C$_{27}$H$_{20}$O$_4$Na [M+Na]$^+$431.1259, found 431.1264.

The identified chemical structure of H-31 is indicated below.

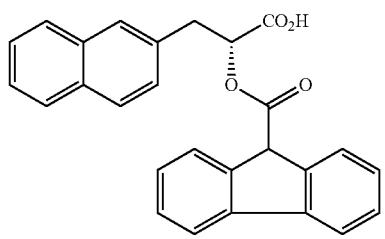

H-31

(Example 2-3) Synthesis of Other Ester Compounds

Multiple ester compounds were synthesized using the intermediate synthesized in Example 2-1 by synthesis methods similar to that in Example 2-2. Then, the inhibitory activity of the synthesized compounds against Pin1 was evaluated by the same evaluation method as that in Example 1-4. The chemical structures and activity evaluation results of the synthesized compounds are shown in the following tables.

TABLE 8

| Compound No. | Structural formula | Pin1 inhibition activity |
|---|---|---|
| H-23 | | ++ |
| H-30 | | ++ |
| H-21 | | − (Hydrolysis causes conversion to H-30, which is active) |
| H-31 | | +++ |

TABLE 8-continued
| Compound No. | Structural formula | Pin1 inhibition activity |
|---|---|---|
| H-141 | 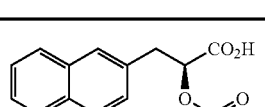 | +++ |
TABLE 9
| Compound No. | Structural formula | Pin1 inhibition activity |
|---|---|---|
| H-32 | | + |
| H-33 | | + |
| H-106 | | ++ |
| H-123 | | ++ |
TABLE 10
| Compound No. | Structural formula | Pin1 inhibition activity |
|---|---|---|
| H-130 | | ++ |
| H-132 | | + |
| H-134 | | ++ |

TABLE 10-continued
| Compound No. | Structural formula | Pin1 inhibition activity |
|---|---|---|
| H-149 | 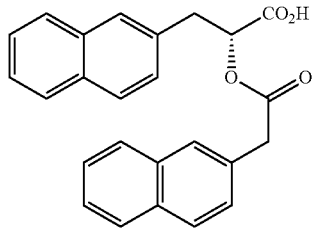 [SMILES: O=C(Cc1ccc2ccccc2c1)O[C@H](Cc1ccc2ccccc2c1)C(=O)O] | + |
| H-151 | 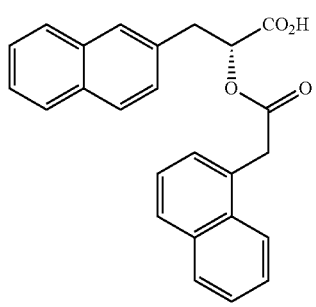 [SMILES: O=C(Cc1cccc2ccccc12)O[C@H](Cc1ccc2ccccc2c1)C(=O)O] | ++ |
TABLE 11
| Compound No. | Structural formula | Pin1 inhibition activity |
|---|---|---|
| H-157 | 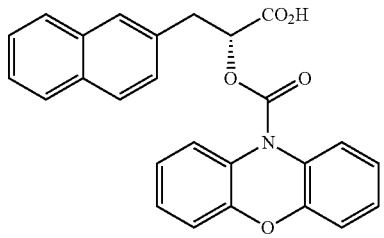 [SMILES: O=C(O)[C@@H](Cc1ccc2ccccc2c1)OC(=O)N1c2ccccc2Oc2ccccc21] | ++ |
| H-175 | 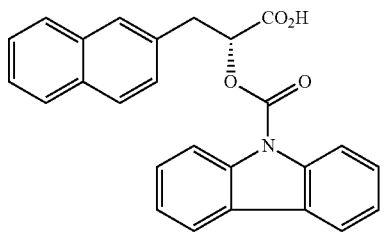 [SMILES: O=C(O)[C@@H](Cc1ccc2ccccc2c1)OC(=O)n1c2ccccc2c2ccccc21] | +++ |
| H-176 | 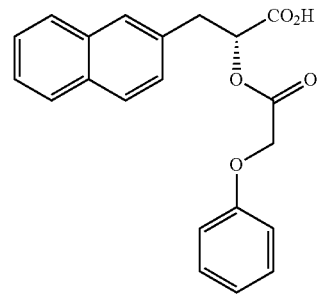 [SMILES: O=C(COc1ccccc1)O[C@H](Cc1ccc2ccccc2c1)C(=O)O] | ++ |
TABLE 11-continued
| Compound No. | Structural formula | Pin1 inhibition activity |
|---|---|---|
| H-177 | 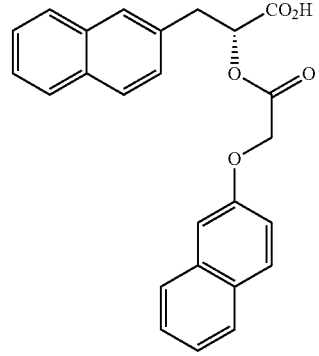 [SMILES: O=C(COc1ccc2ccccc2c1)O[C@H](Cc1ccc2ccccc2c1)C(=O)O] | ++ |
| H-179 | 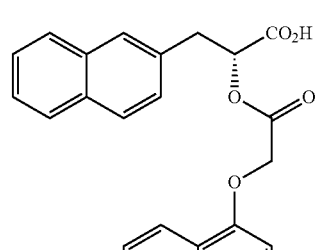 | +++ |
TABLE 12
| Compound No. | Structural formula | Pin1 inhibition activity |
|---|---|---|
| H-180 | | ++ |
| H-198 | | + |
| H-200 | | + |

TABLE 12-continued

| Compound No. | Structural formula | Pin1 inhibition activity |
|---|---|---|
| H-210 | (S)-2-(naphthalen-2-ylmethyl)-2-((3,5-dimethylbenzoyl)oxy)acetic acid | + |
| H-212 | (S)-2-(naphthalen-2-ylmethyl)-2-((4-(dimethylamino)benzoyl)oxy)acetic acid | + |

TABLE 13

| Compound No. | Structural formula | Pin1 inhibition activity |
|---|---|---|
| H-248 | naphthalene derivative with NHBoc-phenylalanine ester | + |
| H-265 | naphthalene derivative with 3,4-dimethylbenzoyl ester | + |
| H-266 | naphthalene derivative with 3,4-dimethoxybenzoyl ester | + |
| H-269 | naphthalene derivative with 3,4-dichlorobenzoyl ester | + |
| H-270 | naphthalene derivative with 3,4-difluorobenzoyl ester | + |

TABLE 14

| Compound No. | Structural formula | Pin1 inhibition activity |
|---|---|---|
| H-254 | naphthalene derivative with 2-methoxyfluorene-9-carbonyl ester | Not measured |
| H-262 | naphthalene derivative with 2-fluorofluorene-9-carbonyl ester | Not measured |

TABLE 14-continued

| Compound No. | Structural formula | Pin1 inhibition activity |
|---|---|---|
| H-263 | | Not measured |
| H-438 | | Not measured |
| H-441 | | Not measured |

TABLE 15

| Compound No. | Structural formula | Pin1 inhibition activity |
|---|---|---|
| H-507 | | Not measured |

TABLE 15-continued

| Compound No. | Structural formula | Pin1 inhibition activity |
|---|---|---|
| H-512 | | Not measured |
| H-514 | | Not measured |
| H-516 | | Not measured |

Example 3

(NASH Treatment Study)

Example 3-1

Animal experiments were performed using non-alcoholic steatohepatitis (NASH) model mice to test the compounds synthesized in Examples for the therapeutic effect on NASH.

NASH model mice (hereinafter referred to as "NASH mice") were produced by feeding a high-fat diet containing trans fatty acids (HFDT) to individual male laboratory mice (C57BL/6J) for 8 weeks. The mice were divided into groups, and animal experiments were performed on a group of mice to which the compound (H-144) synthesized in Example 1-2 or the compound (H-163) synthesized in Example 1-3 was administered intraperitoneally at a dose of 2.5 mg/kg/day three times a week, a group of mice to which H-144 or H-163 was administered orally at a dose of 5.0 mg/kg/day three times a week, a group of mice to which Juglone, a known Pin1 inhibitor, was administered intraperitoneally at a dose of 2.5 mg/kg/day three times a week, a group of mice to which Juglone was administered orally at a dose of 5.0 mg/kg/day three times a week, and a group of mice to which nothing was administered, during the 8-week HFDT feeding period. In addition, a normal diet was given to individual male laboratory mice (C57BL/6J) for 8 weeks to prepare control mice.

The results of measurements of liver weight change, blood ALT (GPT) concentration, and fasting blood glucose in these mice are separately shown in FIG. 1(A) to (C).

FIG. 1 (A) is a graph depicting the result of measurement of mouse liver weight, and graph bars represent the results of measurement of liver weight in the control mice, the NASH mice, the NASH mice treated by intraperitoneal administration of H-163, the NASH mice treated by oral administration of H-163, the NASH mice treated by intraperitoneal administration of H-144, the NASH mice treated by oral administration of H-144, the NASH mice treated by intraperitoneal administration of Juglone, and the NASH mice treated by oral administration of Juglone, from left to right.

As shown in FIG. 1 (A), the liver weight was increased in the NASH mice as a result of fat accumulation in the liver. In contrast, the increase in liver weight was significantly reduced when either H-163 or H-144 was administered. Additionally, the increase in liver weight was significantly reduced in the NASH mice treated by oral administration of Juglone, while the NASH mice treated by intraperitoneal administration of Juglone were all dead within 8 weeks. Severe side effects were suspected to have occurred because of the low specificity of Juglone as a Pin1 inhibitor.

FIG. 1 (B) is a graph depicting the result of measurement of blood ALT (GPT) concentration (IU/ml), and graph bars represent the results of measurement of blood ALT in the control mice, the NASH mice, the NASH mice treated by intraperitoneal administration of H-163, the NASH mice treated by oral administration of H-163, the NASH mice treated by intraperitoneal administration of H-144, the NASH mice treated by oral administration of H-144, the NASH mice treated by intraperitoneal administration of Juglone, and the NASH mice treated by oral administration of Juglone, from left to right.

As shown in FIG. 1 (B), the ALT value, an index of liver inflammation, was increased in the NASH mice given no Pin1 inhibitor. In contrast, the ALT value was decreased and inhibition of liver inflammation was observed when either H-163 or H-144 was administered.

FIG. 1 (C) is a graph depicting the result of measurement of fasting blood glucose concentration (mg/dl), and graph bars represent the results of measurement of fasting blood glucose level in the control mice, the NASH mice, the NASH mice treated by intraperitoneal administration of H-163, the NASH mice treated by oral administration of H-163, the NASH mice treated by intraperitoneal administration of H-144, the NASH mice treated by oral administration of H-144, the NASH mice treated by intraperitoneal administration of Juglone, and the NASH mice treated by oral administration of Juglone, from left to right.

As shown in FIG. 1 (C), the NASH mice treated by intraperitoneal administration of Juglone were all dead within 8 weeks, and the NASH mice treated by oral administration of Juglone were not dead but showed an abnormal increase in blood glucose level. In contrast, no significant abnormality in fasting blood glucose level was detected in the NASH mice given either H-163 or H-144. Juglone is a less specific Pin1 inhibitor and causes severe side effects. In this respect, the compounds according to the present invention were confirmed to have significantly decreased side effects.

Example 3-2

Figure 2:
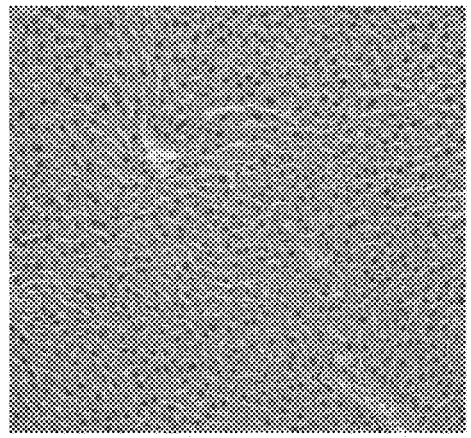
FIG. 2 shows photographs provided instead of drawings and depicting results of microscopic observation of liver tissue sections from mice in a NASH treatment study.
Figure 2:
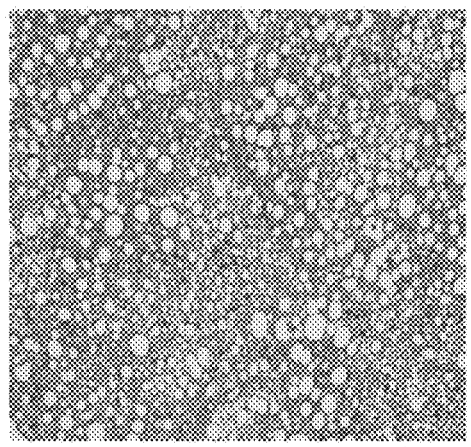
Figure 2:
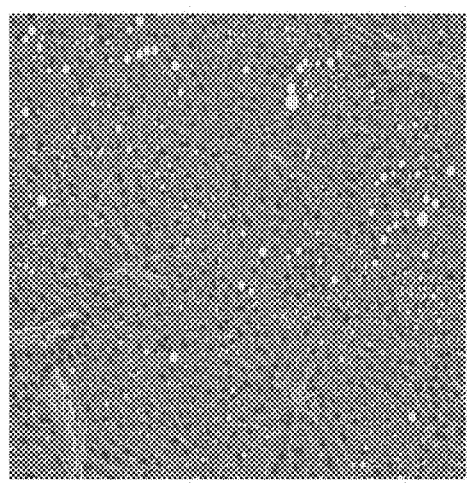

FIG. 2 shows results of microscopic observation of liver tissue sections from the control mice given a normal diet, the NASH mice given a HFDT, and the NASH mice given a HFDT and H-163.

FIG. 2 (A) is a photograph depicting the result of observation of liver tissue from the control mice given a normal diet, and FIG. 2 (B) is a photograph depicting the result of observation of liver tissue from the NASH mice given a HFDT, and FIG. 2 (C) is a photograph depicting the result of observation of liver tissue from the NASH mice given a HFDT and H-163.

No fat accumulation was observed in the liver tissue from the control mice, as shown in FIG. 2 (A), while an accumulation of fat was found in the liver tissue from the NASH mice given a HFDT, as shown in FIG. 2 (B). However, administration of H-163 significantly reduced fat accumulation even in the NASH mice, as shown in FIG. 2 (C).

Example 3-3

Next, an animal experiment was performed on NASH mice that were produced by feeding a methionine-choline-deficient diet (MCDD).

NASH mice were produced by feeding a methionine-choline-deficient diet (MCDD) to individual male laboratory mice (C57BL/6J) for 8 weeks. The mice were divided into groups, and animal experiments were performed on a group of mice to which the compound (H-163) synthesized in Example 1-3 or the compound (H-31) synthesized in Example 2-2 was administered intraperitoneally at a dose of 2.5 mg/kg/day three times a week, and a group of mice to which nothing was administered, during the 8-week MCDD feeding period. In addition, a normal diet was given to individual male laboratory mice (C57BL/6J) for 8 weeks to prepare control mice.

Figure 3:
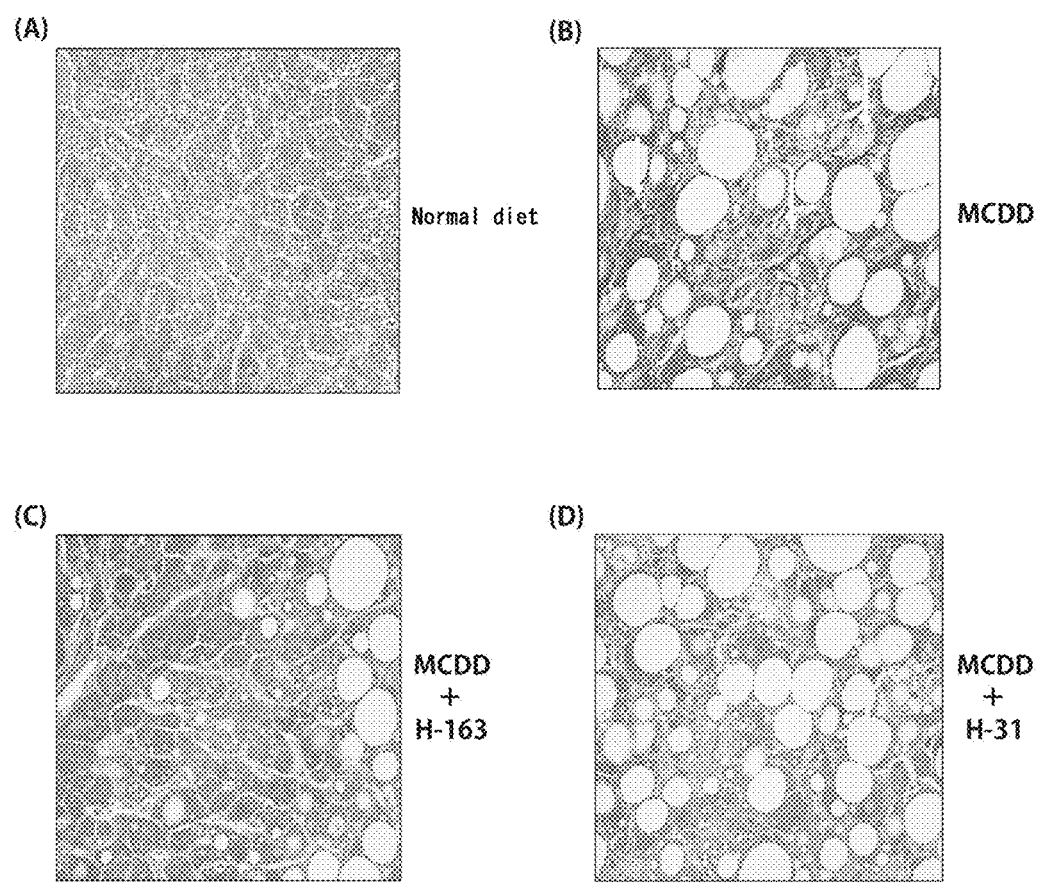
FIG. 3 shows photographs provided instead of drawings and depicting results of microscopic observation of liver tissue sections with Azan staining from mice in a NASH treatment study.

FIG. 3 shows results of microscopic observation of liver tissue sections with Azan staining from those mice.

FIG. 3 (A) is a photograph depicting the result of observation of liver tissue from the control mice, and FIG. 3 (B) is a photograph depicting the result of observation of liver tissue from the NASH mice given a MCDD, and FIG. 3 (C) is a photograph depicting the result of observation of liver tissue from the NASH mice given a MCDD and H-163, and FIG. 3 (D) is a photograph depicting the result of observation of liver tissue from the NASH mice given a MCDD and H-31.

No fat accumulation was observed in the liver tissue from the control mice, as shown in FIG. 3 (A), while an accumulation of fat was found in the liver tissue from the NASH mice given a MCDD, as shown in FIG. 3 (B). In addition, administration of H-163 reduced fat accumulation even in the NASH mice, as shown in FIG. 3 (C). Moreover, as shown in FIG. 3 (B), fibrosis (the colored area pointed by an arrow) was observed in the liver tissue with Azan staining, in the case where H-163 was not administered. In contrast, as shown in FIG. 3 (C) and FIG. 3 (D), hepatic fibrosis was significantly inhibited when either H-163 or H-31 was administered.

Example 3-4

Next, the expression levels of Collagen 1a1 mRNA, Collagen 1a2 mRNA, and SMA mRNA were measured in the control mice given a normal diet, the NASH mice given a MCDD, the NASH mice given a MCDD and H-31, and the NASH mice given a MCDD and H-163. The results are shown in FIG. 4.

Figure 4:
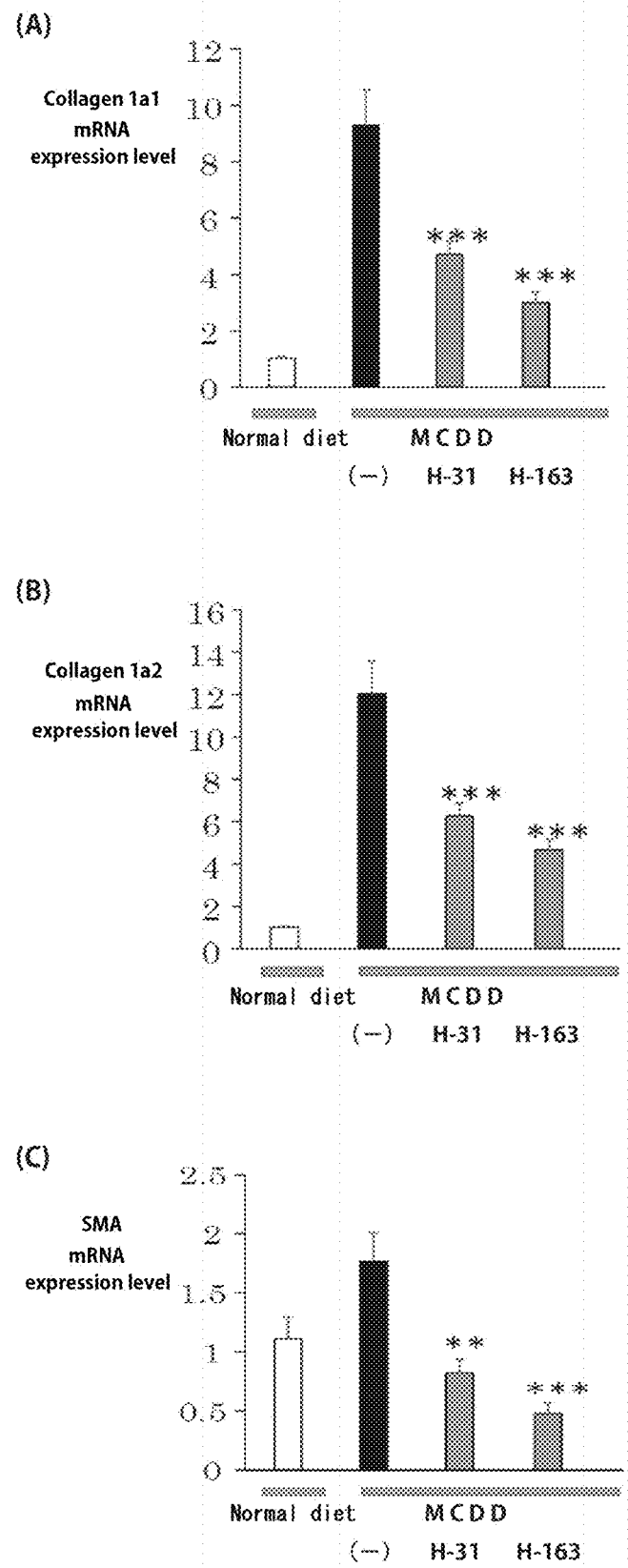
FIG. 4 shows graphs depicting results of measurement of Collagen 1a1 mRNA, Collagen 1a2 mRNA, and SMA mRNA expression levels in a NASH treatment study.

FIG. 4 (A) is a graph depicting the result of measurement of Collagen 1a1 mRNA expression level, and FIG. 4 (B) is a graph depicting the result of measurement of Collagen 1a2 mRNA expression level, and FIG. 4 (C) is a graph depicting the result of measurement of SMA mRNA expression level.

In each graph, graph bars represent the result of measurement of each mRNA expression level in the control mice given a normal diet, the NASH mice given a MCDD, the NASH mice given a MCDD and H-31, and the NASH mice given a MCDD and H-163, from left to right.

As shown in FIGS. 4 (A) to (C), Collagen 1a1, Collagen 1a2, and SMA expression levels, indexes of tissue fibrosis, were increased by feeding of MCDD. However, administration of H-31 or H-163 reduced the expression levels of these genes, which was indicated to inhibit fibrosis.

INDUSTRIAL APPLICABILITY

The therapeutic or prophylactic agents for fatty liver disease and for obesity according to the present invention are each useful in the pharmaceutical industry.

The invention claimed is:

1. A therapeutic or prophylactic agent for the treatment or prevention of fatty liver disease, comprising a compound represented by the Formula (I) or a pharmaceutically acceptable salt thereof as an active ingredient:

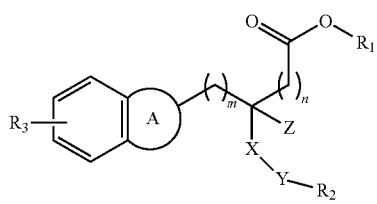

wherein m represents an integer of 0 to 2, and n represents an integer of 0 to 1, provided that $0 \leq m+n \leq 2$;

a ring A represents a benzene ring and forms a naphthyl group with adjacent benzene ring;

X represents —O—CO— group;

Y represents a single bond, —NH— group, —CH$_2$—O— group, —CH$_2$— group, or —CH(NH—Boc)—CH$_2$— group;

Z represents a hydrogen atom;

$R_1$ represents a hydrogen atom, an optionally substituted hydrocarbon group, an optionally substituted heterocyclic group, or an optionally substituted amino group;

$R_2$ represents an optionally substituted aryl group, an optionally substituted heterocyclic group, an optionally substituted cycloalkyl group, or a group represented by the following Formula (II):

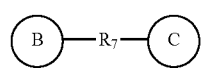

wherein rings B and C independently represent an optionally substituted aryl group, an optionally substituted heterocyclic group, or an optionally substituted cycloalkyl group, and $R_7$ represents a single bond, —O— group, —CO— group, —NH— group, —SO$_2$— group, —CO—NH— group, an optionally substituted C$_{1-3}$ alkylene group, an optionally substituted C$_{2-3}$ alkenylene group, —S—R$_8$— group wherein $R_8$ represents an optionally substituted C$_{1-2}$ alkylene group, —CO—R$_8$— group, —O—R$_8$— group, or —SO$_2$—R$_8$—group, and Y is attached to any of the ring B, ring C, and $R_7$; and $R_3$ represents 0 to 4 identical or different substituents.

2. The therapeutic or prophylactic agent according to claim 1, wherein the fatty liver disease is non-alcoholic steatohepatitis.

3. The therapeutic or prophylactic agent according to claim 1, wherein m is 1 and n is 0.

4. The therapeutic or prophylactic agent according to claim 1, wherein $R_2$ represents an optionally substituted polycyclic aryl group or an optionally substituted polycyclic heterocyclic group.

5. The therapeutic or prophylactic agent according to claim 1, wherein Y represents a single bond, —CH$_2$— group, or —CH$_2$—O— group.

6. The therapeutic or prophylactic agent according to claim 1, wherein $R_1$ represents a hydrogen atom.

7. The therapeutic or prophylactic agent according to claim 1, further comprising an active ingredient of at least one additional drug for the treatment or prevention of fatty liver disease.

8. A method of treating or preventing fatty liver disease, comprising administering the therapeutic or prophylactic agent according to claim 1, in combination with at least one additional drug for the treatment or prevention of fatty liver disease.

9. A therapeutic or prophylactic agent for the treatment or prevention of obesity, comprising a compound represented by the Formula (I) or a pharmaceutically acceptable salt thereof as an active ingredient:

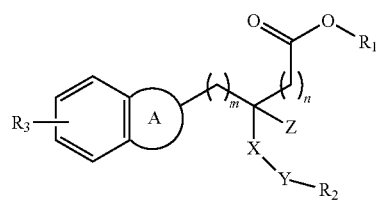

wherein m represents an integer of 0 to 2, and n represents an integer of 0 to 1, provided that $0 \leq m+n \leq 2$;

a ring A represents a benzene ring and forms a naphthyl group with adjacent benzene ring;

X represents —O—CO— group;

Y represents a single bond, —NH— group, CH$_2$—O— group, —CH$_2$— group, or —CH(NH—Boc)—CH$_2$— group;

Z represents a hydrogen atom;

$R_1$ represents a hydrogen atom, an optionally substituted hydrocarbon group, an optionally substituted heterocyclic group, or an optionally substituted amino group;

$R_2$ represents an optionally substituted aryl group, an optionally substituted heterocyclic group, an optionally substituted cycloalkyl group, or a group represented by the following Formula (II):

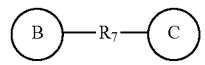 (II)

wherein rings B and C independently represent an optionally substituted aryl group, an optionally substituted heterocyclic group, or an optionally substituted cycloalkyl group, and $R_7$ represents a single bond, —O— group, —CO— group, —NH— group, —$SO_2$— group, —CO—NH— group, an optionally substituted $C_{1-3}$ alkylene group, an optionally substituted $C_{2-3}$ alkenylene group, —S—$R_8$— group wherein $R_8$ represents an optionally substituted $C_{1-2}$ alkylene group, —CO—$R_8$— group, —O—$R_8$— group, or —$SO_2$—$R_8$— group, and Y is attached to any of the ring B, ring C, and $R_7$; and $R_3$ represents 0 to 4 identical or different substituents.

10. The therapeutic or prophylactic agent according to claim 9, wherein m is 1 and n is 0.

11. The therapeutic or prophylactic agent according to claim 9, wherein $R_2$ represents an optionally substituted polycyclic aryl group or an optionally substituted polycyclic heterocyclic group.

12. The therapeutic or prophylactic agent according to claim 9, wherein Y represents a single bond, —$CH_2$— group, or —$CH_2$—O— group.

13. The therapeutic or prophylactic agent according to claim 9, wherein $R_1$ represents a hydrogen atom.

14. The therapeutic or prophylactic agent according to claim 9, further comprising an active ingredient of at least one additional drug for the treatment or prevention of obesity.

15. A method of treating or preventing obesity, comprising administering the therapeutic or prophylactic agent according to claim 9 in combination with at least one additional drug for the treatment or prevention of obesity.

* * * * *